US012622627B2

(12) United States Patent
Liu et al.

(10) Patent No.: US 12,622,627 B2
(45) Date of Patent: May 12, 2026

(54) ELECTROENCEPHALOGRAM SIGNAL CLASSIFICATION METHOD AND APPARATUS, DEVICE, STORAGE MEDIUM AND PROGRAM PRODUCT

(71) Applicant: TENCENT TECHNOLOGY (SHENZHEN) COMPANY LTD, Guangdong (CN)

(72) Inventors: Luyan Liu, Shenzhen (CN); Kai Ma, Shenzhen (CN); Yefeng Zheng, Shenzhen (CN)

(73) Assignee: TENCENT TECHNOLOGY (SHENZHEN) COMPANY LTD, Shenzhen (CN)

( * ) Notice: Subject to any disclaimer, the term of this patent is extended or adjusted under 35 U.S.C. 154(b) by 769 days.

(21) Appl. No.: 17/977,519

(22) Filed: Oct. 31, 2022

(65) Prior Publication Data

US 2023/0075309 A1     Mar. 9, 2023

Related U.S. Application Data

(63) Continuation of application No. PCT/CN2022/077619, filed on Feb. 24, 2022.

(30) Foreign Application Priority Data

Feb. 26, 2021    (CN) .......................... 202110220638.6

(51) Int. Cl.
 *A61B 5/374*        (2021.01)
 *A61B 5/00*         (2006.01)
 *G06F 3/01*         (2006.01)
(52) U.S. Cl.
 CPC ............ *A61B 5/374* (2021.01); *A61B 5/7267* (2013.01); *G06F 3/015* (2013.01)

(58) Field of Classification Search
 None
 See application file for complete search history.

(56) References Cited

U.S. PATENT DOCUMENTS 11,157,082 B2 * 10/2021 Mureşan ................. G06F 3/015
2014/0058528 A1 * 2/2014 Contreras-Vidal .... A61B 5/374
                                                        600/383
(Continued)

FOREIGN PATENT DOCUMENTS

CN      108245763 A      7/2018
CN      110531861 A      12/2019
(Continued)

OTHER PUBLICATIONS

"EEG-Based Brain-Computer Interface for Decoding Motor Imagery Tasks within the Same Hand Using Choi-Williams Time-Frequency distributions"; Rami Alazrai, Hisham Alwanni, Yara Baslan, Nasim Alnuman and Mohammad I. Daoud; Biomedical Sensors and Systems 2017; Aug. 23, 2017 (Year: 2017).*
(Continued)

*Primary Examiner* — Michael Alsip
(74) *Attorney, Agent, or Firm* — Sughrue Mion, PLLC

(57) ABSTRACT

An electroencephalogram (EEG) signal classification method and apparatus, a device, a storage medium, and a program product are provided, and relate to the field of signal processing technologies. The method includes: obtaining a first EEG signal; obtaining time-frequency feature maps of at least two electrode signals in the first EEG signal; performing feature extraction based on the time-frequency feature maps of the at least two electrode signals to obtain a first extracted feature map; performing weighting processing based on an attention mechanism on the first (Continued)

extracted feature map to obtain an attention feature map; and obtaining a motor imagery type of the first EEG signal based on the attention feature map.

18 Claims, 9 Drawing Sheets

(56) References Cited

U.S. PATENT DOCUMENTS

| 2014/0369537 | A1* | 12/2014 | Pontoppidan | ........ | H04R 25/606 |
| | | | | | 381/314 |
| 2016/0242690 | A1* | 8/2016 | Principe | ................ | A61B 5/316 |
| 2019/0066713 | A1* | 2/2019 | Mesgarani | .............. | G10L 25/30 |
| 2019/0332931 | A1 | 10/2019 | Montantes | | |
| 2021/0077005 | A1* | 3/2021 | Ambeck-Madsen | .... | A61B 5/18 |

FOREIGN PATENT DOCUMENTS

| CN | 110610168 | A | 12/2019 |
| CN | 111012336 | A | 4/2020 |
| CN | 111110230 | A | 5/2020 |
| CN | 111317468 | A | 6/2020 |
| CN | 111714118 | A | 9/2020 |
| CN | 111728609 | A | 10/2020 |
| CN | 112022152 | A | 12/2020 |
| CN | 112244774 | A | 1/2021 |
| CN | 112257658 | A | 1/2021 |
| CN | 113693613 | A | 11/2021 |
| CN | 111184511 | A | 5/2022 |

OTHER PUBLICATIONS

"EEG and Deep Learning Based Brain Cognitive Function Classification"; Saraswati Sridhar and Vidya Manian; Dec. 21, 2020 (Year: 2020).*

Office Action issued Feb. 26, 2024 in Chinese Application No. 202110220638.6.

Translation of the International Search Report issued May 25, 2022 in International Application No. PCT/CN2022/077619.

Translation of the Written Opinion issued May 25, 2022 in International Application No. PCT/CN2022/077619.

Jun Yang et al., "Multichannel MI-EEG Feature Decoding Based on Deep Learning", Journal of Electronics & Information Technology, vol. 43 No. 1, Jan. 2021, pp. 196-203.

Sanghyun Woo et al., "CBAM: Convolutional Block Attention Module", Korea Advanced Institute of Science and Technology, ECCV, 2018, pp. 1-17.

Written Opinion of PCT/CN2022/077619 dated May 25, 2022.

International Search Report for PCT/CN2022/077619 dated May 25, 2022.

Communication dated Jun. 14, 2024 issued by the European Patent Office in application No. 22758912.4.

Guangyi Zhang, et al., "RFNet: Riemannian Fusion Network for EEG-based Brain-Computer Interfaces", arXiv:2008.08633v1 [cs. CV], Aug. 19, 2020, pp. 1-12.

Dalin Zhang, et al. "A Graph-Based Hierarchical Attention Model for Movement Intention Detection from EEG Signals", IEEE Transactions on Neural Systems and Rehabilitation Engineering, vol. 27, No. 11, Nov. 2019, pp. 2247-2253.

Chen-Chen Fan, et al., "Bilinear neural network with 3-D attention for brain decoding of motor imagery movements from the human EEG", Cognitive Neurodynamics, vol. 15, No. 1, 2021, pp. 181-189.

Dalin Zhang, et al., "Motor Imagery Classification via Temporal Attention Cues of Graph Embedded EEG Signals", IEEE Journal of Biomedical and Health Informatics, vol. 24, No. 9, Sep. 2020, pp. 2570-2579.

* cited by examiner

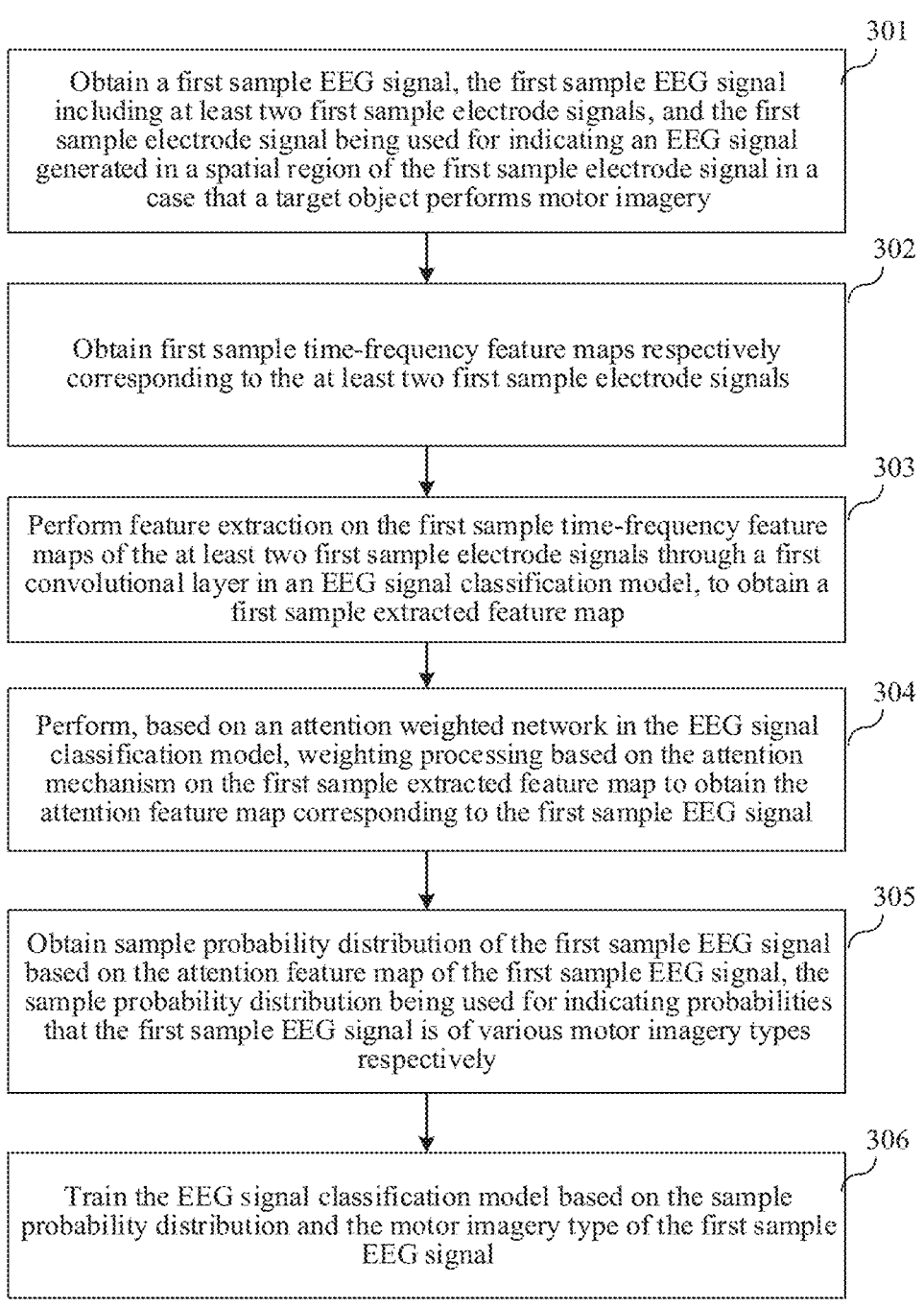

301

Obtain a first sample EEG signal, the first sample EEG signal including at least two first sample electrode signals, and the first sample electrode signal being used for indicating an EEG signal generated in a spatial region of the first sample electrode signal in a case that a target object performs motor imagery

302

Obtain first sample time-frequency feature maps respectively corresponding to the at least two first sample electrode signals

303

Perform feature extraction on the first sample time-frequency feature maps of the at least two first sample electrode signals through a first convolutional layer in an EEG signal classification model, to obtain a first sample extracted feature map

304

Perform, based on an attention weighted network in the EEG signal classification model, weighting processing based on the attention mechanism on the first sample extracted feature map to obtain the attention feature map corresponding to the first sample EEG signal

305

Obtain sample probability distribution of the first sample EEG signal based on the attention feature map of the first sample EEG signal, the sample probability distribution being used for indicating probabilities that the first sample EEG signal is of various motor imagery types respectively

306

Train the EEG signal classification model based on the sample probability distribution and the motor imagery type of the first sample EEG signal

FIG. 3

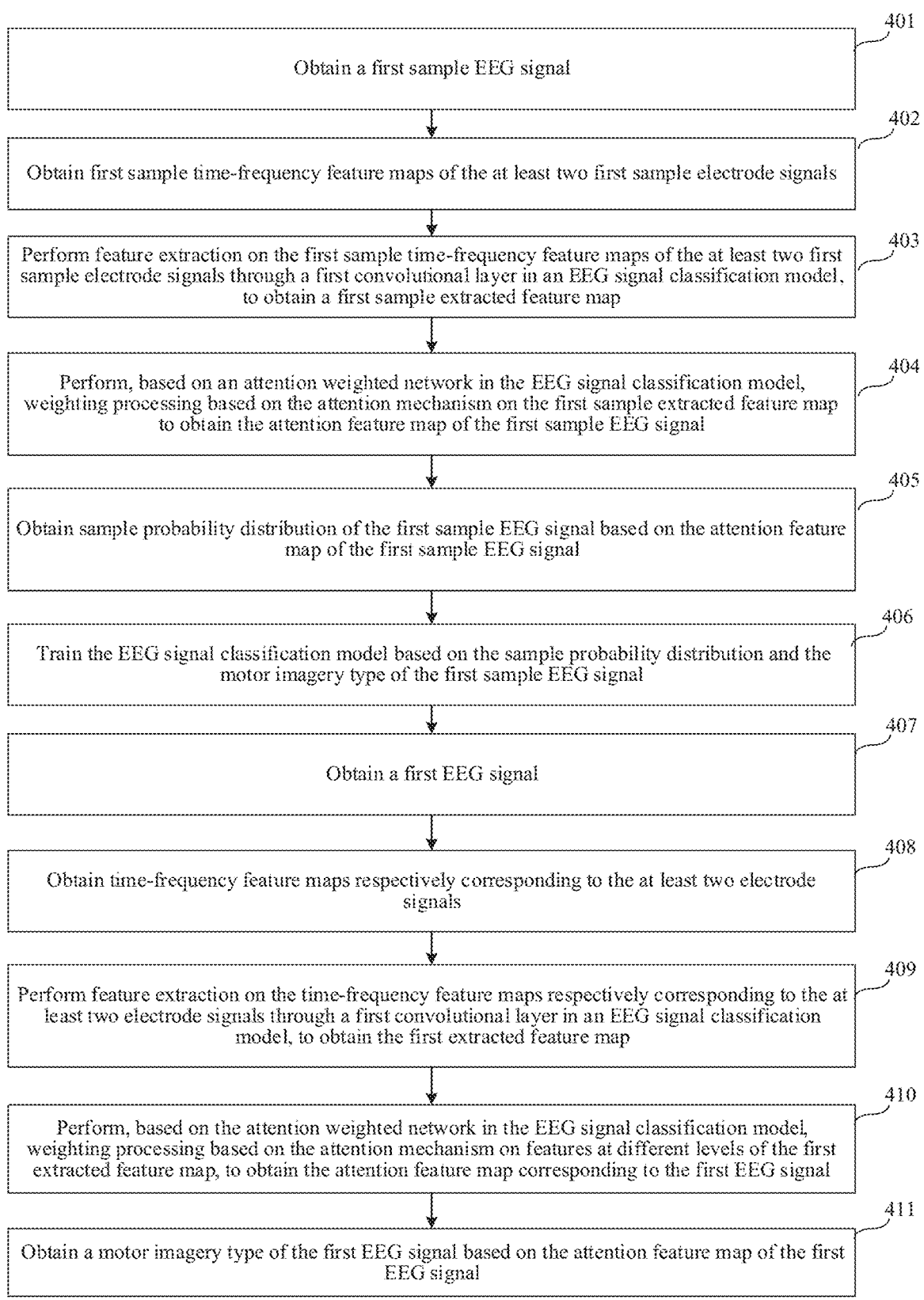

401 Obtain a first sample EEG signal

402 Obtain first sample time-frequency feature maps of the at least two first sample electrode signals 403 Perform feature extraction on the first sample time-frequency feature maps of the at least two first sample electrode signals through a first convolutional layer in an EEG signal classification model, to obtain a first sample extracted feature map 404 Perform, based on an attention weighted network in the EEG signal classification model, weighting processing based on the attention mechanism on the first sample extracted feature map to obtain the attention feature map of the first sample EEG signal 405 Obtain sample probability distribution of the first sample EEG signal based on the attention feature map of the first sample EEG signal 406 Train the EEG signal classification model based on the sample probability distribution and the motor imagery type of the first sample EEG signal 407 Obtain a first EEG signal 408 Obtain time-frequency feature maps respectively corresponding to the at least two electrode signals 409 Perform feature extraction on the time-frequency feature maps respectively corresponding to the at least two electrode signals through a first convolutional layer in an EEG signal classification model, to obtain the first extracted feature map 410 Perform, based on the attention weighted network in the EEG signal classification model, weighting processing based on the attention mechanism on features at different levels of the first extracted feature map, to obtain the attention feature map corresponding to the first EEG signal 411 Obtain a motor imagery type of the first EEG signal based on the attention feature map of the first EEG signal

FIG. 4

ELECTROENCEPHALOGRAM SIGNAL CLASSIFICATION METHOD AND APPARATUS, DEVICE, STORAGE MEDIUM AND PROGRAM PRODUCT

CROSS-REFERENCE TO RELATED APPLICATION(S)

This application is a continuation application of International Application No. PCT/CN2022/077619, filed Feb. 24, 2022, which claims priority to Chinese Patent Application No. 202110220638.6, filed on Feb. 26, 2021, the disclosures of which are herein incorporated by reference in their entireties.

FIELD

The disclosure relates to the field of signal processing technologies, and in particular, to an electroencephalogram signal classification method and apparatus, a device, a storage medium, and a program product.

BACKGROUND

Electroencephalogram (EEG) records changes of electric waves during brain activity, and is the overall reflection of electrophysiological activities of brain nerve cells in the cerebral cortex or scalp surface.

In the related art, a motor imagery-brain computer interface (MI-BCI) system has a wide application prospect in many fields, through which an external device can be controlled through electroencephalogram signals generated by imagining limb movements in the brain without any actual limb movements. Classification and recognition for motor imagery (MI) signals is a key operation in the MI-BCI system.

SUMMARY

Embodiments of the disclosure provide an electroencephalogram (EEG) signal classification method and apparatus, a device, a storage medium, and a program product. The technical solutions are as follows:

According to an aspect of an example embodiment, an EEG signal classification method is provided, and performed by at least one processor. The method includes:

obtaining a first EEG signal, the first EEG signal including at least two electrode signals, an electrode signal of the at least two electrode signals indicating an EEG signal generated by a target object in a spatial region corresponding to the electrode signal;

obtaining time-frequency feature maps of the at least two electrode signals, a time-frequency feature map indicating a time-domain feature and a frequency-domain feature of the electrode signal;

performing feature extraction based on the time-frequency feature maps of the at least two electrode signals to obtain a first extracted feature map, the first extracted feature map being fused with spatial features of the at least two electrode signals, and the spatial features of the at least two electrode signals being related to spatial regions corresponding to the at least two electrode signals;

performing weighting processing based on an attention mechanism on the first extracted feature map to obtain an attention feature map of the first EEG signal; and obtaining a motor imagery type of the first EEG signal based on the attention feature map of the first EEG signal.

According to an aspect of an example embodiment, an EEG signal classification method is provided, and performed by at least one processor. The method includes:

obtaining a first sample EEG signal, the first sample EEG signal including at least two first sample electrode signals, and a first sample electrode signal indicating an EEG signal generated in a spatial region corresponding to the first sample electrode signal from a target object that performs motor imagery;

obtaining first sample time-frequency feature maps of the at least two first sample electrode signals, a first sample time-frequency feature map indicating a time-domain feature and a frequency-domain feature of a corresponding first sample electrode signal;

performing feature extraction on the first sample time-frequency feature maps of the at least two first sample electrode signals through a first convolutional layer in an EEG signal classification model, to obtain a first sample extracted feature map, the first sample extracted feature map being fused with spatial features of the at least two first sample electrode signals, and the spatial features of the at least two first sample electrode signals being related to spatial regions corresponding to the at least two first sample electrode signals;

performing, based on an attention weighted network in the EEG signal classification model, weighting processing based on an attention mechanism on the first sample extracted feature map to obtain an attention feature map of the first sample EEG signal;

obtaining a sample probability distribution of the first sample EEG signal based on the attention feature map of the first sample EEG signal, the sample probability distribution indicating probabilities that the first sample EEG signal is of each of a plurality of motor imagery types, respectively; and training the EEG signal classification model based on the sample probability distribution and a motor imagery type of the first sample EEG signal, the EEG signal classification model being configured to predict a motor imagery type of a first EEG signal.

According to an aspect of an example embodiment, an EEG signal classification apparatus is provided. The apparatus includes:

at least one memory configured to store program code; and at least one processor configured to read the program code and operate as instructed by the program code, the program code including:

first signal obtaining code configured to cause the at least one processor to obtain a first EEG signal; the first EEG signal including at least two electrode signals, and an electrode signal indicating an EEG signal generated by a target object in a spatial region corresponding to the electrode signal;

first time-frequency feature obtaining code configured to cause the at least one processor to obtain time-frequency feature maps of the at least two electrode signals, a time-frequency feature map indicating a time-domain feature and a frequency-domain feature of the electrode signal;

first extracted feature obtaining code configured to cause the at least one processor to perform feature extraction based on the time-frequency feature maps of the at least two electrode signals to obtain a first extracted feature map, the first extracted feature map being fused with spatial features of the at least two electrode signals, and the spatial features of the at least two electrode signals being related to spatial regions corresponding to the at least two electrode signals;

first attention feature obtaining code configured to cause the at least one processor to perform weighting processing based on an attention mechanism on the first extracted feature map to obtain an attention feature map of the first EEG signal; and imagery type obtaining code configured to cause the at least one processor to obtain a motor imagery type of the first EEG signal based on the attention feature map of the first EEG signal.

According to an aspect of an example embodiment, an EEG signal classification apparatus is provided. The apparatus includes:

at least one memory configured to store program code; and at least one processor configured to read the program code and operate as instructed by the program code, the program code including:

first sample obtaining code configured to cause the at least one processor to obtain a first sample EEG signal, the first sample EEG signal including at least two first sample electrode signals, and a first sample electrode signal indicating an EEG signal generated in a spatial region of the first sample electrode signal in a case that a target object performs motor imagery;

first sample time-frequency obtaining code configured to cause the at least one processor to obtain first sample time-frequency feature maps of the at least two first sample electrode signals, a first sample time-frequency feature map indicating a time-domain feature and a frequency-domain feature of the first sample electrode signal;

first sample extraction obtaining code configured to cause the at least one processor to perform feature extraction on the first sample time-frequency feature maps of the at least two first sample electrode signals through a first convolutional layer in an EEG signal classification model, to obtain a first sample extracted feature map, the first sample extracted feature map being fused with spatial features of the at least two first sample electrode signals, and the spatial features of the at least two first sample electrode signals being related to spatial regions of the at least two first sample electrode signals;

first sample attention obtaining code configured to cause the at least one processor to perform, based on an attention weighted network in the EEG signal classification model, weighting processing based on the attention mechanism on the first sample extracted feature map to obtain the attention feature map of the first sample EEG signal;

first sample probability obtaining code configured to cause the at least one processor to obtain sample probability distribution of the first sample EEG signal based on the attention feature map of the first sample EEG signal, the sample probability distribution indicating probabilities that the first sample EEG signal is of various motor imagery types respectively; and first training code configured to cause the at least one processor to train the EEG signal classification model based on the sample probability distribution and the motor imagery type of the first sample EEG signal, the EEG signal classification model being configured to predict the motor imagery type corresponding to the first EEG signal.

According to an aspect of an example embodiment, a computer device is provided. The computer device includes a processor and a memory, the memory storing at least one computer instruction, and the at least one computer instruction being loaded and executed by the processor to implement the foregoing EEG signal classification method.

According to an aspect of an example embodiment, a non-transitory computer-readable storage medium is provided. The storage medium stores at least one computer instruction, the at least one computer instruction being loaded and executed by a processor to implement the foregoing EEG signal classification method.

According to an aspect of an example embodiment, a computer program product or a computer program is provided, including a computer instruction, the computer instructions being stored in a computer-readable storage medium. A processor of a computer device reads the computer instruction from the computer-readable storage medium and executes the computer instruction to cause the computer device to perform the foregoing EEG signal classification method.

BRIEF DESCRIPTION OF THE DRAWINGS

FIG. 3 is a schematic flowchart of an EEG signal classification method according to an example embodiment.

FIG. 4 is a method flowchart of an EEG signal classification method according to an example embodiment.

DETAILED DESCRIPTION

Hereinafter, example embodiments of the disclosure are described with reference to the accompanying drawings.

An electroencephalogram (EEG) signal classification method provided in embodiments of the disclosure may be applied to a computer device having a data processing capability. In an example embodiment, the EEG signal classification method provided in the embodiments of the disclosure may be applied to a personal computer, a workstation, or a server. That is, training of an EEG signal classification model may be performed through the personal computer, the workstation, or the server. In an example embodiment, the EEG signal classification model trained by using the EEG signal classification method provided in the embodiments of the disclosure may be applied to classification of an EEG signal. That is, data processing is performed on an obtained EEG signal generated by a head during human motor imagery, to obtain a motor imagery type corresponding to the EEG signal.

Figure 1:
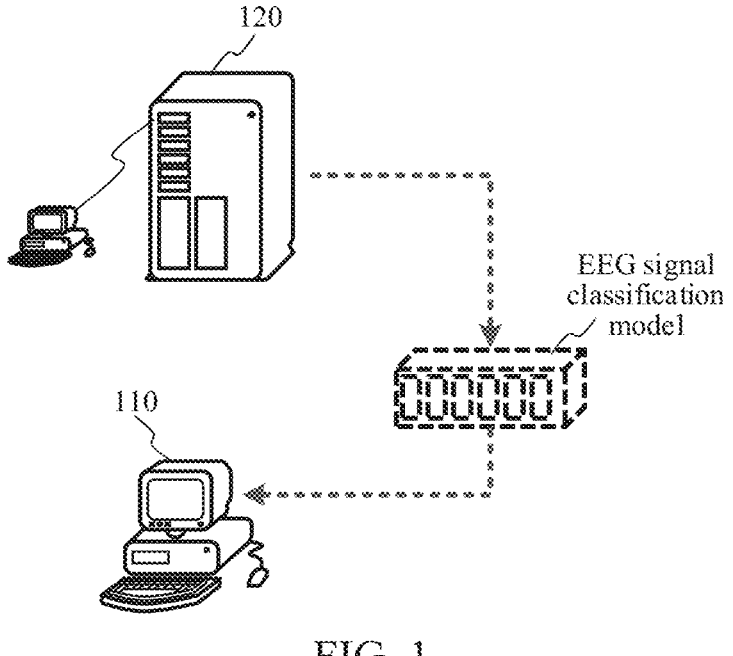
FIG. 1 is a schematic diagram of a computer system according to an example embodiment of the disclosure.

FIG. 1 is a schematic diagram of a computer system according to an example embodiment of the disclosure. A computer system includes a terminal 110 and a server 120. The terminal 110 is in data communication with the server 120 through a communication network. The communication network may be a wired network or a wireless network, and the communication network may be at least one of a local area network, a metropolitan area network, and a wide area network.

An application having an EEG signal processing function is mounted in the terminal 110. The application may be a virtual reality application, a game application, or an artificial intelligence (AI) application having the EEG signal processing function. This is not limited in the embodiments of the disclosure.

The terminal 110 may be a terminal device having a brain-computer interface (BCI). The BCI may obtain an EEG signal from a head of a target object through an electrode. Alternatively, the computer device includes a data transmission interface for receiving an EEG signal acquired by a data acquisition device having the BCI.

The terminal 110 may be a mobile terminal such as a smart phone, a tablet computer, or a portable laptop computer, or may be a terminal such as a desktop computer, a projection computer, or a smart terminal having a data processing component. This is not limited in the embodiments of the disclosure.

The server 120 may be implemented as a server or may be implemented as a server cluster formed by a set of servers, and may be a physical server or may be implemented as a cloud server. In an example embodiment, the server 120 is a backend server of the application in the terminal 110.

In an example embodiment, the server 120 trains the EEG signal classification model through a preset training sample set (e.g., a sample EEG signal). The training sample set may include sample EEG signals corresponding to a plurality of motor imagery types. After completing a training process of the EEG signal classification model, the server 120 transmits a trained EEG signal classification model to the terminal 110 through a wired or wireless connection. The terminal 110 receives the trained EEG signal classification model, and inputs data information corresponding to the EEG signal classification model into the application having the EEG signal processing function, so that when using the application to process the EEG signal, a user may process the EEG signal according to the trained EEG signal classification model, to implement all or part of operations of the EEG signal classification method.

Figure 2:
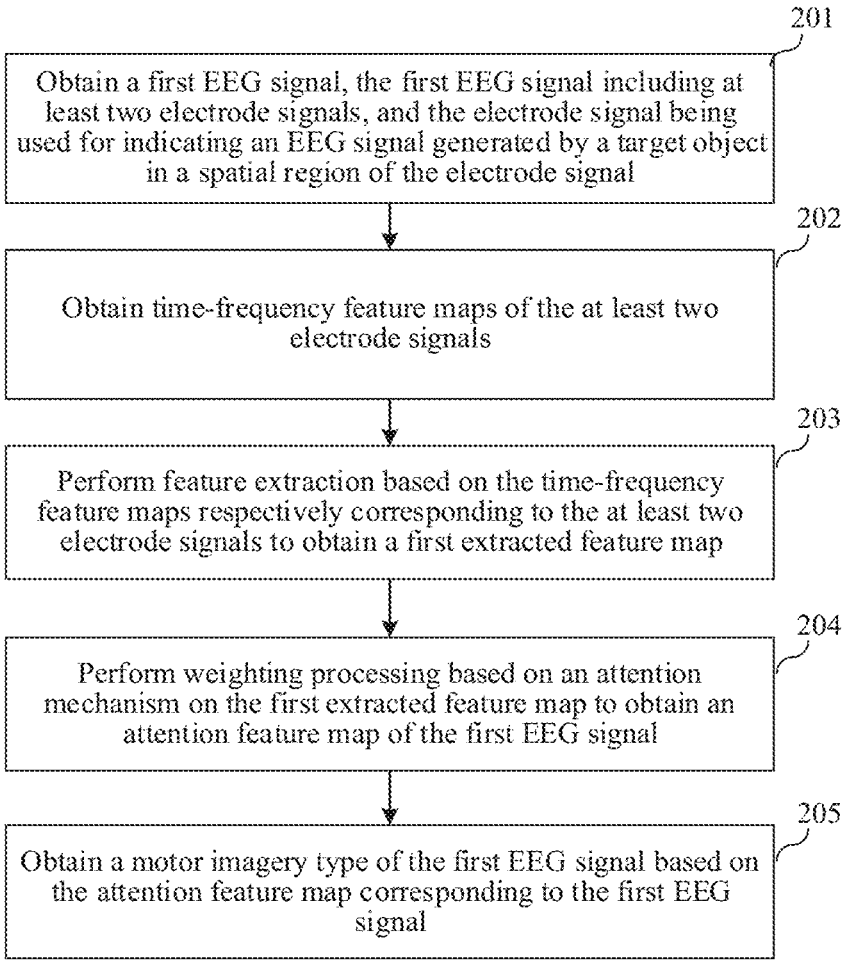
FIG. 2 is a schematic flowchart of an EEG signal classification method according to an example embodiment.

FIG. 2 is a schematic flowchart of an EEG signal classification method according to an example embodiment. The method may be performed by a computer device. The computer device may be the terminal 110 or the server 120 in the embodiments shown in FIG. 1. As shown in FIG. 2, a flow of the EEG signal classification method may include the following operations 201-205:

Operation 201. Obtain a first EEG signal, the first EEG signal including at least two electrode signals, and the electrode signal being used for indicating an EEG signal generated by a target object in a spatial region of the electrode signal.

The spatial region of the electrode signal refers to a spatial region corresponding to the electrode signal.

In an example embodiment, the first EEG signal is an EEG signal of the target object acquired by a device having the BCI. The BCI includes at least two electrodes. During a process that signal acquisition is performed on the target object through the BCI, the two electrodes are located in different spatial regions of a head of the target object, so as to acquire EEG signals generated by the target object in different spatial regions.

Operation 202. Obtain time-frequency feature maps of the at least two electrode signals.

The time-frequency feature map may indicate a time-domain feature and a frequency-domain feature of the electrode signal.

Operation 203. Perform feature extraction based on the time-frequency feature maps respectively corresponding to the at least two electrode signals to obtain a first extracted feature map.

The first extracted feature map is fused with spatial features of the at least two electrode signals, and the spatial features of the at least two electrode signals are related to spatial regions of the at least two electrode signals.

Because the first extracted feature map is obtained by feature extraction based on the time-frequency feature maps of the at least two electrode signals, and the spatial regions of the at least two electrode signals are different, the computer device considers the spatial regions respectively corresponding to the at least two electrode signals when performing feature extraction based on the time-frequency feature maps of the at least two electrode signals. Because the fused first extracted feature map is obtained based on the time-frequency feature maps respectively corresponding to the at least two electrode signals, the first extracted feature map is fused with information related to the spatial region indicated by the at least two electrode signals, that is, fused with the spatial features of the at least two electrode signals.

Operation 204. Perform weighting processing based on an attention mechanism on the first extracted feature map to obtain an attention feature map of the first EEG signal.

In an example embodiment, the computer device may perform weighting processing on features at different levels in the first extracted feature map based on the attention mechanism, to obtain the attention feature map of the first EEG signal.

The features at different levels in the first extracted feature map may be used for indicating features obtained by using different feature extraction methods in the first extracted feature map.

For example, the computer device performs feature extraction on the first extracted feature map by using a first feature extraction method to obtain a first level feature, and information in the first level feature corresponds to the first feature extraction method. Then, the computer device performs feature extraction on the first level feature by using a second feature extraction method to obtain a second level feature. In this case, the second level feature is obtained by performing feature extraction by using the first feature extraction method and the second feature extraction method based on the first extracted feature map. Thus, information in the second level feature includes features of the first feature extraction method and the second feature extraction method.

Operation 205. Obtain a motor imagery type of the first EEG signal based on the attention feature map corresponding to the first EEG signal.

In the embodiments of the disclosure, the attention feature map of the first EEG signal is obtained based on the time-frequency feature maps corresponding to the at least two electrode signals, and the at least two electrode signals are used for indicating EEG signals generated by the target object in different spatial regions, so that the attention feature map has certain spatial features, that is, the extracted attention feature map takes into account time-domain features, frequency-domain features and spatial-domain features.

According to the solutions shown in the embodiments of the disclosure, an EEG signal including at least two electrode signals is obtained, and a time-frequency feature map is obtained according to the at least two electrode signals. The time-frequency feature map may indicate a time-domain feature and a frequency-domain feature of the electrode signal. Then, feature extraction is performed on the time-frequency feature map to obtain a first extracted feature map, and features at different levels of the extracted first extracted feature map are weighted based on an attention mechanism, to obtain a weighted attention feature map. Finally a motor imagery type of the EEG signal is determined based on the weighted attention feature map. In the foregoing solution, the time-frequency feature map is a time-frequency feature map of EEG signals generated by the target object in different electrode signal regions. That is, the time-frequency feature map further includes a spatial relationship between different electrode signals. Therefore, feature extraction is performed on the time-frequency feature map through the EEG signal classification model, through which the time-domain feature and frequency-domain feature of the EEG signal may be considered at the same time. The feature map extracted from the time-frequency feature map is weighted through the attention mechanism, through which a spatial relationship between at least two electrode signals of the EEG signal may be considered. Therefore, the attention feature map finally obtained is a feature extracted by fusing a time-domain feature, a frequency-domain feature, and a spatial-domain feature of the EEG signal at the same time. To ensure diversification of image feature levels, positions of rich features in the feature map may be paid more attention through the attention mechanism. Therefore, accuracy of predicting the motor imagery type of the EEG signal may be improved by determining the motor imagery type of the first EEG signal through the attention feature map.

FIG. 3 is a schematic flowchart of an EEG signal classification method according to an example embodiment. The method may be performed by a computer device. The computer device may be the terminal 110 or the server 120 in the embodiments shown in FIG. 1. As shown in FIG. 3, a flow of the EEG signal classification method may include the following operations 301-306:

Operation 301. Obtain a first sample EEG signal, the first sample EEG signal including at least two first sample electrode signals, and the first sample electrode signal being used for indicating an EEG signal generated in a spatial region of the first sample electrode signal in a case that a target object performs motor imagery.

The first sample EEG signal is used for training the EEG signal classification model, and the first sample EEG signal may indicate an EEG signal generated in a region of the sample electrode signal when the sample target object performs motor imagery, so that the EEG signal classification model trained by using the first sample EEG signal may be used for analyzing the motor imagery type of the EEG signal.

Operation 302. Obtain first sample time-frequency feature maps respectively corresponding to the at least two first sample electrode signals.

The first sample time-frequency feature map may indicate a time-domain feature and a frequency-domain feature of the first sample electrode signal.

Operation 303. Perform feature extraction on the first sample time-frequency feature maps of the at least two first sample electrode signals through a first convolutional layer in an EEG signal classification model, to obtain a first sample extracted feature map.

The first sample extracted feature map is fused with spatial features of the at least two first sample electrode signals, and the spatial features of the at least two first sample electrode signals are related to spatial regions of the at least two first sample electrode signals.

Operation 304. Perform, based on an attention weighted network in the EEG signal classification model, weighting processing based on the attention mechanism on the first sample extracted feature map to obtain the attention feature map corresponding to the first sample EEG signal.

Operation 305. Obtain sample probability distribution of the first sample EEG signal based on the attention feature map of the first sample EEG signal, the sample probability distribution being used for indicating probabilities that the first sample EEG signal is of each of various motor imagery types respectively.

Operation 306. Train the EEG signal classification model based on the sample probability distribution and the motor imagery type of the first sample EEG signal.

The EEG signal classification model is used for predicting the motor imagery type of the first EEG signal based on the first EEG signal.

According to the solutions shown in the embodiments of the disclosure, the time-frequency feature map is a time-frequency feature map corresponding to EEG signals generated by the target object in regions corresponding to different electrode signals. That is, the time-frequency feature map further includes a spatial relationship between different electrode signals. Therefore, feature extraction is performed on the time-frequency feature map through the trained EEG signal classification model, through which the time-domain feature and frequency-domain feature of the EEG signal may be considered at the same time. The feature map extracted from the time-frequency feature map is weighted through the attention mechanism, through which a spatial relationship between at least two electrode signals of the EEG signal may be considered. Therefore, the attention feature map finally obtained is a feature extracted by fusing a time-domain feature, a frequency-domain feature, and a spatial-domain feature of the EEG signal at the same time. To ensure diversification of image feature levels, positions of rich features in the feature map may be paid more attention through the attention mechanism. Therefore, accuracy of predicting the motor imagery type of the EEG signal may be improved by determining the motor imagery type corresponding to the first EEG signal through the attention feature map.

FIG. 4 is a method flowchart of an EEG signal classification method according to an example embodiment. The method may be jointly performed by a model training device and a signal processing device. For example, subsequent operations 401 to 406 may be performed by the model training device and operations 407 to 411 may be performed by the signal processing device. The model training device may be the server 120 in the foregoing embodiment shown in FIG. 1 and the signal processing device may be the terminal 110 in the foregoing embodiment shown in FIG. 1. As shown in FIG. 4, a flow of the EEG signal classification method may include the following operations 401-411:

Operation 401. Obtain a first sample EEG signal.

The first sample EEG signal includes at least two first sample electrode signals.

In an example embodiment, the at least two first sample electrode signals of the first sample EEG signal may be EEG signals generated in a head of a sample target object during motor imagery, and obtained through a sample acquisition device (e.g. a terminal device) having a BCI through an electrode of the BCI. A quantity of the first sample electrode signals is the same as a quantity of electrodes corresponding to the BCI. That is, the BCI may obtain EEG signals generated in different spatial regions of a head of a same sample target object during motor imagery through different electrodes, and provide the acquired EEG signals as sample EEG signals to the model training device.

In an example embodiment, the BCI obtains EEG signals generated in different regions of the head of the sample target object through electrodes connected to the sample target object, and the electrodes connected to the sample target object transmit EEG signals corresponding to each electrode to a terminal device corresponding to the BCI through a transmission line.

In an example embodiment, the sample acquisition device may obtain an original sample EEG signal generated in the head of the sample target object during motor imagery based on each electrode of the BCI, and obtain the first sample EEG signal by performing filtering processing through a band-pass filter based on the original sample EEG signal.

Because there are many noises in the original sample EEG signal obtained through the electrode of the BCI, the sample acquisition device/model training device may filter the original sample EEG signal through the band-pass filter, to reduce an influence of irrelevant noises on the EEG signal.

In an example embodiment, the sample acquisition device/model training device performs band-pass filtering processing of 3 to 38 Hz on each original sample EEG signal, to remove an influence caused by an irrelevant physiological noise such as an eye movement and a power frequency interference (e.g., an interference caused by a power system, which is usually 50 HZ) on the EEG signal.

Operation 402. Obtain first sample time-frequency feature maps of the at least two first sample electrode signals.

In an example embodiment, the model training device may respectively perform a normalization operation on the at least two first sample electrode signals in the first sample EEG signal to obtain at least two sample standard signals, and obtain the first sample time-frequency feature map based on the at least two sample standard signals.

After band-pass filtering processing of 3 to 38 HZ is performed on each original sample EEG signal, the irrelevant physiological noise and power frequency interference may be filtered out, to obtain the first sample EEG signal. Because there may still be noise that cannot be removed by band-pass filtering in the first sample EEG signal, the at least two sample electrode signals of the first sample EEG signal may be normalized in order to reduce signal disturbance caused by noise. The normalization operation may include, for example but not limited to, any one of an exponentially weighted moving average operation, a mean variance normalization, and a common spatial pattern algorithm.

In an example embodiment, the model training device may perform continuous wavelet transform (CWT) based on the at least two first sample electrode signals, and obtain the first sample time-frequency feature maps respectively corresponding to the at least two first sample electrode signals.

The CWT is a kind of operation through which a signal is decomposed into components in different frequencies changing with time. Although Fourier transform and a discrete form thereof discrete Fourier transform (DFT) have become most commonly used tools in signal processing, especially in time-frequency analysis, the Fourier transform has a problem that time-domain and frequency-domain information of the signal cannot be localized at the same time. A continuous wavelet convolves a function (whose integral from negative infinity to positive infinity is zero) that may be called a wavelet with a to-be-processed signal at a certain scale. Changing a scale of the wavelet function will change a band-pass range of a filter, and accordingly, a wavelet coefficient at each scale reflects information of a corresponding passband. In essence, the continuous wavelet is a set of multiscale filters with a controllable passband range.

When the first sample EEG signal is processed through the CWT, the first sample EEG signal may be fitted through a basis function corresponding to the CWT. Unlike the Fourier transform, a wavelet basis corresponding to the CWT is affected by both time and frequency. Therefore, the first sample time-frequency feature map obtained by performing the CWT based on the two first sample electrode signals of the first sample EEG signal, includes both the time-domain feature of the first sample electrode signal in the first sample EEG signal and the frequency-domain feature of the first sample electrode signal in the first sample EEG signal.

In the embodiments of the disclosure, a wavelet basis function corresponding to the CWT may be cmor3.0-3.0, and the wavelet basis function may further be any one of haar wavelet, db wavelet, sym wavelet, and coif series wavelet.

In an example embodiment, the CWT is performed based on the at least two first sample electrode signals to obtain time-frequency feature maps respectively corresponding to the at least two first sample electrode signals. The time-frequency feature map may indicate a time-domain feature and a frequency-domain feature of the sample electrode signal. Based on the first sample time-frequency feature maps respectively corresponding to the at least two first sample electrode signals, the time-frequency feature map corresponding to the first sample EEG signal is obtained.

The first sample EEG signal may include at least two sample electrode signals, that is, the first sample EEG signal includes EEG signals generated in at least two regions of a head of the sample target object during motor imagery by the BCI through at least two electrodes. In this case, the model training device may respectively perform the CWT on the at least two sample electrode signals, obtain the time-frequency feature maps respectively corresponding to the at least two sample electrode signals, and then splice the time-frequency feature maps respectively corresponding to the at least two sample electrode signals according to a channel, to obtain the time-frequency feature map corresponding to the first sample EEG signal.

In convolutional neural network (CNN), the channel may be used for indicating a feature map, strength of a point in the channel may represent a numerical value of the feature map at the point, and different channels are used for indicating feature maps in different dimensions. A feature map with a plurality of channels means that the feature map has image features in a plurality of dimensions. There are two main operations in a convolutional network, which are convolution and pooling. A pooling layer does not affect interaction between channels, but operates in each channel. However, a convolutional layer may interact between channels, and then generate a new channel in a next layer.

The time-frequency feature map corresponding to the first sample EEG signal has image features of at least two channels. The image features of the at least two channels respectively correspond to the first sample time-frequency feature maps of the at least two electrodes. That is, the time-frequency feature map corresponding to the first sample EEG signal is formed based on the first sample time-frequency feature maps corresponding to at least two electrodes, and each channel in the time-frequency feature map corresponding to the first sample EEG signal respectively corresponds to a first sample time-frequency feature map corresponding to each electrode.

In an example embodiment, image features of each channel in the time-frequency feature map corresponding to the first sample EEG signal are respectively determined according to signal images of the time-frequency feature maps of the at least two electrodes. That is, when the time-frequency feature maps corresponding to the at least two sample electrode signals are obtained, the model training device may obtain the time-frequency feature maps corresponding to the at least two sample electrode signals according to the time-frequency feature maps respectively corresponding to the at least two sample electrode signals, and splice the time-frequency feature maps corresponding to the at least two first sample electrode signals according to channels, to obtain the time-frequency feature map corresponding to the first sample EEG signal. In this case, the time-frequency feature map corresponding to the first sample EEG signal includes time-domain features and frequency-domain features of EEG signals generated in different regions of the head of the sample target object during motor imagery.

Figure 5:
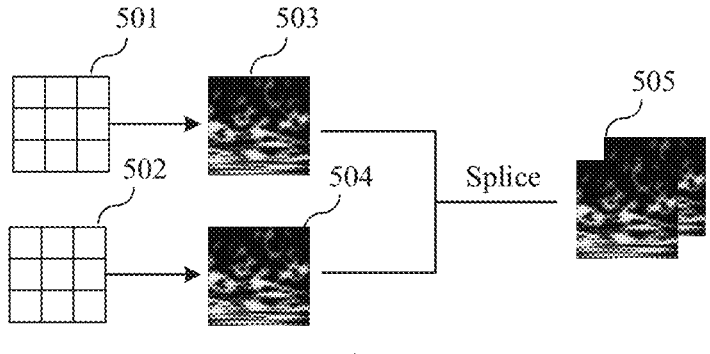
FIG. 5 is a schematic diagram of channel scale splicing of a time-frequency feature map used in the embodiment of FIG. 4.

FIG. 5 is a schematic diagram of channel scale splicing of a time-frequency feature map used in the embodiments of the disclosure. As shown in FIG. 5, using an example in which the first EEG signal includes EEG signals generated in two regions of a head of the target object during motor imagery and obtained through two electrodes, the CWT is performed on a first electrode signal 501 corresponding to the first EEG signal, to obtain a first time-frequency feature map 503 corresponding to the first electrode signal. The CWT is performed on a second electrode signal 502 corresponding to the first EEG signal, to obtain a second time-frequency feature map 504 corresponding to the second electrode signal 502. Channel scales of the first time-frequency feature map 503 and the second time-frequency feature map 504 are spliced according to the channels, to obtain a time-frequency feature map 505 corresponding to a first EEG signal having two channels to save all features of the first time-frequency feature map 503 and the second time-frequency feature map 504.

Operation 403. Perform feature extraction on the first sample time-frequency feature maps of the at least two first sample electrode signals through a first convolutional layer in an EEG signal classification model, to obtain a first sample extracted feature map.

The first sample time-frequency feature maps respectively corresponding to the at least two first sample electrode signals may be obtained by performing feature extraction through the first convolutional layer in the EEG signal classification model.

In an example embodiment, image features of each channel in the first sample extracted feature map may include image features of the first sample time-frequency feature map of each of the at least two first sample electrode signals, that is, include image features of each channel in the first sample time-frequency feature map.

For example, when the first convolutional layer includes 3*3 convolutional kernels, and a quantity of the convolutional kernels is 5, each convolutional kernel in the first convolutional layer is summed after performing a convolution operation with each channel in the first sample time-frequency feature map, to obtain an image feature corresponding to the convolutional kernel. Therefore, when the five convolutional kernels respectively perform the convolution operation with the first sample time-frequency feature map, image features of five channels may be obtained, that is, a first sample extracted feature map whose channel is 5. In addition, because image features in each channel in the first sample extracted feature map are summed according to the convolution operation of each channel, the image features in each channel include image features of each channel in the first sample time-frequency feature map. That is, feature extraction is performed on the first sample time-frequency feature map through the first convolutional layer, and time-frequency features of each channel in the first sample time-frequency feature map are fused. In addition, because each channel in the time-frequency feature map corresponding to the first EEG signal is an EEG signal of the sample object acquired by electrodes at different positions, the fused first sample extracted feature map is fused with features of at least two electrode signals. Spatial features of the at least two sample electrode signals are related to the spatial regions of the at least two sample electrode signals, so that the fused first sample extracted feature map is a feature map with a time-domain feature, a frequency-domain feature, and a spatial feature at the same time.

Operation 404. Perform, based on an attention weighted network in the EEG signal classification model, weighting processing based on the attention mechanism on the first sample extracted feature map to obtain the attention feature map of the first sample EEG signal.

In an example embodiment, based on the attention weighted network in the EEG signal classification model, weighting processing based on the attention mechanism is performed on features at different levels of the first sample extracted feature map, to obtain the attention feature map corresponding to the first sample EEG signal.

The features at different levels in the first sample extracted feature map may be used for indicating features obtained after feature extraction through different convolutional layers in the first sample extracted feature map.

Figure 6:
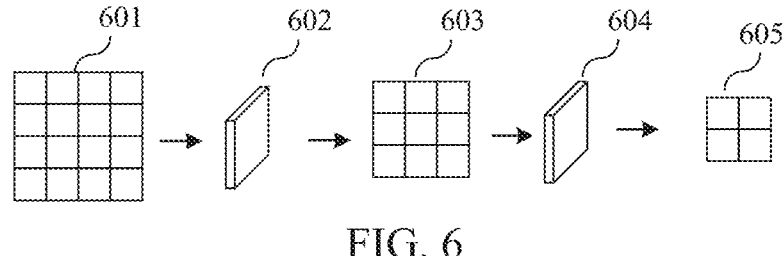
FIG. 6 is a schematic diagram of a feature hierarchy used in the embodiment of FIG. 4.

FIG. 6 is a schematic diagram of a feature hierarchy used in the embodiments of the disclosure. As shown in FIG. 6, after feature extraction is performed on a feature map 601 through the first convolutional layer 602, a first level feature map 603 is obtained, and the first level feature map 603 may be used for indicating features corresponding to the feature map 601 and the first convolutional layer 602. After feature extraction is performed on the first level feature map 603 through a second convolutional layer 604, a second level feature map 605 is obtained. The second level feature map 605 is obtained by sequentially performing feature extraction on the feature map 601 through the first convolutional layer 602 and the second convolutional layer 604, so that the second level feature map may indicate features corresponding to the first convolutional layer 602 and the second convolutional layer 604 at the same time of the feature map, and the second level feature map and the first level feature map are features at different levels.

In an example embodiment, the attention mechanism includes at least one of a spatial attention mechanism and a channel attention mechanism.

Figure 7:
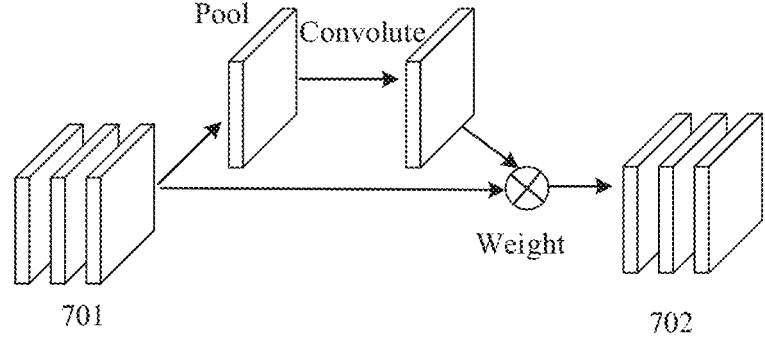
FIG. 7 is a schematic diagram of a spatial attention mechanism used in the embodiment of FIG. 4.

FIG. 7 is a schematic diagram of a spatial attention mechanism used in the embodiments of the disclosure. As shown in FIG. 7, for a feature map 701 whose channel is C and size is W×H, an average feature map is obtained by averaging feature maps of all channels. The average feature map is transformed through a learnable convolutional layer to transform to form a spatial attention value. Finally, the spatial attention value is multiplied by all channel feature maps to form a spatial attention feature map 702.

Because the spatial attention mechanism is an average feature map averaged based on feature maps of each channel and according to each region in the feature map, and finally, an average feature map integrating features of the feature maps of each channel is obtained. The average feature map may indicate a region with most features in feature maps with different channels and a same size. Therefore, a spatial attention feature map obtained by weighting all channel feature maps through the spatial attention value formed by the average feature map pays more attention to a region with rich features in each feature map.

Figure 8:
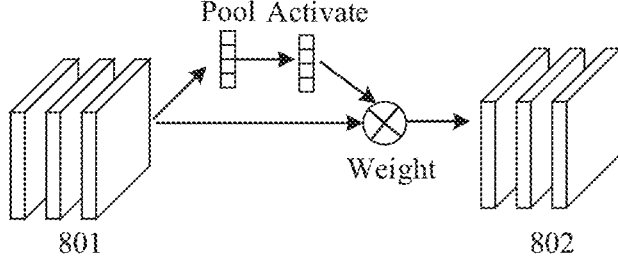
FIG. 8 is a schematic diagram of a channel attention mechanism used in the embodiment of FIG. 4.

FIG. 8 is a schematic diagram of a channel attention mechanism used in the embodiments of the disclosure. As shown in FIG. 8, for a feature map 801 whose channel is C and size is W×H, firstly, mean-pooling is performed on each feature map to obtain a feature map mean corresponding to C channels. The mean corresponding to each channel is mapped through a fully connected layer to form a channel attention value, and an activation function of the fully connected layer is a sigmoid function. Finally, a channel attention value corresponding to each channel is multiplied (e.g. weighted) with a corresponding channel feature map to form a channel attention feature map 802.

Because through the channel attention mechanism, a mean corresponding to each channel is mapped into a channel attention value through the fully connected layer, an attention feature map obtained by weighting according to the channel attention value pays more attention to a channel with a larger mean (that is, an image feature of a channel with a larger mean has larger weight).

In an example embodiment, the first attention weighted network includes a first spatial attention weighted network, a second convolutional layer, a first channel attention network, and a third convolutional layer. The model training device may perform, based on the first spatial attention weighted network, weighting processing based on the spatial attention mechanism on the first sample extracted feature map to obtain a first sample spatial feature map; perform feature extraction on the first sample spatial feature map based on the second convolutional layer to obtain a second sample extracted feature map; perform, based on the first channel attention weighted network, weighting processing based on the channel attention mechanism on the second sample extracted feature map to obtain a first sample channel feature map; perform feature extraction on the first sample channel feature map based on the third convolutional layer to obtain a third sample extracted feature map; and obtain the attention feature map corresponding to the first sample EEG signal based on the first sample spatial feature map, the first sample channel feature map, and the third sample extracted feature map.

The first sample spatial feature map is obtained by performing weighting processing based on the spatial attention mechanism on the first sample extracted feature map, and accordingly, a feature in the first sample spatial feature map pays more attention to a position where image features are rich in each image channel. Based on the second convolutional layer, the second sample extracted feature map obtained by performing feature extraction on the first sample spatial feature map is a feature at different levels from the first sample spatial feature map. Therefore, the first sample channel feature map obtained by performing weighting processing on the second sample extracted feature map through the channel attention mechanism is also a feature at different levels from the first sample spatial feature map. Based on the third convolutional layer, the third sample extracted feature map obtained by performing feature extraction on the first sample channel feature map is a feature map different from the first sample channel feature map, and at different levels from the first sample spatial feature map. That is, the first sample spatial feature map, the first sample channel feature map, and the third sample extracted feature map are image features at different levels and obtained by using different feature extraction methods based on the first sample extracted feature map.

Therefore, the attention feature map is obtained based on image features at different levels, and by weighting through a spatial attention weighting mechanism and a channel attention weighting mechanism respectively. That is, the attention feature map corresponding to the first sample EEG signal includes image features at different levels at the same time, and the image features at different levels are weighted through the attention mechanism, so that the attention feature map corresponding to the first sample EEG signal includes a time-domain feature, a frequency-domain feature, a spatial-domain feature, and further includes the attention mechanism. After weighting processing is performed by using different convolutional kernels, the features at different levels are extracted, and the attention feature map has image features at more levels. In addition, on a basis of ensuring diversification of image feature levels, positions of rich features in the feature map may be paid more attention to through the attention mechanism, thereby improving an effect of feature extraction.

In an example embodiment, the first attention weighted network further includes the second attention weighted network. The model training device may fuse the first sample spatial feature map, the first sample channel feature map, and the third sample extracted feature map to obtain a first sample fused feature map. Based on the first sample fused feature map, weight processing based on the attention mechanism is performed through the second attention weighted network, to obtain the attention feature map corresponding to the first sample EEG signal.

The first sample fused feature map is obtained by fusing the first sample spatial feature map, the first sample channel feature map, and the third sample extracted feature map, so that the first sample fused feature map includes image features at three different levels at the same time. The model training device may, based on the first sample fused feature map, perform weighting processing on the first sample fused feature map through the second attention weighted network. The attention feature map obtained is further weighted through the attention mechanism based on the first sample fused feature map, so that an important feature in the fused first sample fused feature map is further strengthened, and a feature extraction effect is improved.

In an example embodiment, the second attention weighted network includes at least one of the second spatial attention weighted network and the second channel attention weighted network.

In an example embodiment, the second attention weighted network includes the second spatial attention weighted network and the second channel attention weighted network. The model training device may perform weighting processing based on the channel attention mechanism on the first sample fused feature map through the second channel attention weighted network, to obtain the second sample channel feature map, and perform weighting processing based on the spatial attention mechanism on the second sample channel feature map through the second sample spatial attention weighted network, to obtain the attention feature map corresponding to the first sample EEG signal.

When the second attention weighted network includes the second spatial attention weighted network, the model training device may pay more attention to a region where features are rich in each feature map according to the attention feature map obtained by performing weighting on the first sample extracted feature map by the spatial attention weighted network. When the attention weighted network includes the second channel attention weighted network, the model training device may pay more attention to a channel where features are rich in the feature map according to the attention feature map obtained by performing weighting on the first sample extracted feature map by the channel attention weighted network. Therefore, the first sample fused feature map is processed through the second attention weighted network, which may further perform weighting on the first sample fused feature map through the channel attention mechanism and the spatial attention mechanism, so that the feature map may pay more attention to a part where information is rich on a channel scale and a spatial scale.

Operation 405. Obtain sample probability distribution of the first sample EEG signal based on the attention feature map of the first sample EEG signal.

In an example embodiment, the model training device may obtain a feature vector of the first sample EEG signal based on the attention feature map corresponding to the first sample EEG signal, and obtain sample probability distribution of the first sample EEG signal based on the feature vector corresponding to the first sample EEG signal.

In an example embodiment, the EEG signal classification model further includes a first fully connected layer. The model training device may perform data processing through the first fully connected layer based on the attention feature map corresponding to the first sample EEG signal to obtain the feature vector corresponding to the first sample EEG signal.

The model training device may input the attention feature map corresponding to the first sample EEG signal to the first fully connected layer, to obtain the feature vector corresponding to the first sample EEG signal. Sizes of values of different dimensions in the feature vector indicate possibility that the first sample EEG signal corresponds to different motor imagery types.

In an example embodiment, the model training device may input the feature vector corresponding to the first sample EEG signal to a softmax activation layer of the EEG signal classification model, to obtain the sample probability distribution corresponding to the first sample EEG signal.

Operation 406. Train the EEG signal classification model based on the sample probability distribution and the motor imagery type of the first sample EEG signal.

In an example embodiment, the model training device may obtain a second sample EEG signal. The second sample EEG signal includes at least two second sample electrode signals, and the second sample electrode signal may indicate an EEG signal generated in a spatial region corresponding to the second sample electrode signal in a case that a target object performs motor imagery. The model training device may obtain second sample time-frequency feature maps respectively corresponding to the at least two second sample electrode signals based on the at least two second sample electrode signals. The second sample time-frequency feature map may indicate a time-domain feature and a frequency-domain feature corresponding to the second sample electrode signal. The model training device may perform feature extraction on the second sample time-frequency feature maps respectively corresponding to the at least two second sample electrode signals through the first convolutional layer in the EEG signal classification model, to obtain the second sample extracted feature map. The second sample extracted feature map is fused with spatial features of the at least two second sample electrode signals, and the spatial features of the at least two second sample electrode signals are related to spatial regions of the at least two second sample electrode signals. The model training device may perform, based on the attention weighted network in the EEG signal classification model, weighting processing based on the attention mechanism on the second sample extracted feature map to obtain the attention feature map corresponding to the second sample EEG signal. The model training device may train the EEG signal classification model based on the sample probability distribution and the motor imagery type of the first sample EEG signal. The EEG signal classification model may be used for predicting the motor imagery type corresponding to the first EEG signal based on the first EEG signal.

A process of performing feature extraction on the second sample EEG signal through the EEG signal classification model to obtain a feature vector corresponding to the second sample EEG signal may be similar to a process of performing feature extraction on the first sample EEG signal through the EEG signal classification model to obtain the feature vector corresponding to the first sample EEG signal. This is not repeated herein.

In an example embodiment, the model training device may obtain a first loss function value based on the sample probability distribution and the motor imagery type of the first sample EEG signal, obtain a second loss function value based on the feature vector of the first sample EEG signal and the feature vector of the second sample EEG signal, and train the EEG signal classification model based on the first loss function value and the second loss function value.

In an example embodiment, the model training device may input the feature vector corresponding to the first sample EEG signal and the feature vector corresponding to the second sample EEG signal to a domain discriminator in the EEG signal classification model to obtain the second loss function value.

The domain discriminator may be a convolutional layer structure in transfer learning, and may be used for obtaining an outputted matrix according to input, and determining whether a sample is positive or negative according to a mean of the outputted matrix. In the embodiments of the disclosure, the domain discriminator may be used to determine whether an inputted second sample EEG signal and the first sample EEG signal are EEG signals of a same type.

The transfer learning is a machine learning method, and is to use a model developed for Task A as an initial point and reuse it in a process of developing a model for Task B. The transfer learning is a machine learning method, and means that a pre-trained model is reused in another task. The transfer learning is very popular for some problems in deep learning, such as cases that there are a large quantity of resources required to train a deep model or a large quantity of data sets used for pre-training a model. The transfer learning only works when a deep model feature in a first task is a generalization feature. This transfer in the deep learning is called inductive transfer, that is, to narrow a search range for possible models in an advantageous manner by using a model applicable to different but associated tasks.

In an example embodiment of the disclosure, the model training process includes three part of loss functions: a classifier loss function, a domain discriminator loss function, and an overall loss function.

The classifier loss function may be as follows:

$$L_c(\theta_f, \theta_c) = E_{(x_i^s, y_i^s) \sim \mathcal{D}_s} L(p_i^s, y_i^s)$$

$$p_i^s \text{ and } y_i^s$$

are respectively a true label and prediction probability of source domain data (e.g., the first sample EEG signal), L represents a cross entropy loss function, and $\theta_f$ and $\theta_c$ respectively represent a feature extractor parameter and a classifier parameter. E represents probability distribution that the source domain data $$(x_i^s, y_i^s)$$

are respectively each type of motor imagery $\mathcal{D}_s$.

The domain discriminator loss function may be as follows:

$$L_d(\theta_f, \theta_d) = -E_{x_i^s \sim D_s} \log[D(f_i^s)] - E_{x_j^t \sim D_t} \log[1 - D(f_j^t)]$$

$$f_i^s \text{ and } f_j^t$$

are respectively a source domain feature and a target domain feature. The domain discriminator loss function updates the model according to a value outputted by the discriminator, and the domain discriminator is used for respectively determining probabilities that the inputted first sample EEG signal and second sample EEG signal are a source domain and a target domain. $E_{x_i^s \sim D_s}$ represents a probability distribution that the first sample EEG signal is the source domain, $E_{x_j^t \sim D_t}$ represents a probability distribution that the second sample EEG signal is the target domain, and D is output of the discriminator. The model may simultaneously learn features of the source domain and the target domain through the domain discriminator.

An overall loss function of the model may be:

$$L_d(\theta_f, \theta_c, \theta_d) = L_c - \alpha L_d$$

$\alpha$ is a hyperparameter of a balance classification loss $L_c$ and a discriminator loss $L_d$. According to the overall loss function of the model, the model improves classification performance by classifying a value of the loss function, and learns the features of the source domain and the target domain. Therefore, the model may ensure that the model may have a certain capability to classify and recognize the inputted second sample EEG signal in a case that there are no tags in the target domain (e.g., the second sample EEG signal), which improve generalization of model training.

In an example embodiment, the second sample EEG signal may indicate EEG signals generated by a target object corresponding to the first sample EEG signal at different moments, or the second sample EEG signal may indicate an EEG signal generated by a human body other than the target object corresponding to the first sample EEG signal.

When the second sample EEG signal is an EEG signal generated by a sample target object of the first sample EEG signal performing the motor imagery at different moments, the first sample EEG signal may be used as source domain data in adversarial learning, and the second sample EEG signal may be used as target domain data in the adversarial learning. The model is trained through a motor imagery type corresponding to the first sample EEG signal and a sample probability distribution corresponding to the first sample EEG signal, which may improve a capability of the model to classify the motor imagery type. When the feature vector corresponding to the first sample EEG signal and the feature vector corresponding to the second sample EEG signal are inputted into the domain discriminator, and the model is trained through the loss function, because the second sample EEG signal is EEG data generated when the target object performs motor imagery at different moments (or different times), the trained model has a good recognition degree for EEG signals triggered by a same human body at different moments, which improves time invariance of the trained model for EEG recognition.

When the second sample EEG signal and the first sample EEG signal are EEG signals generated by different sample target objects performing the motor imagery at different moments, the first sample EEG signal may be used as source domain data in adversarial learning, and the second sample EEG signal may be used as target domain data in the adversarial learning. The model is trained through a motor imagery type corresponding to the first sample EEG signal and a sample probability distribution corresponding to the first sample EEG signal, which may improve a capability of the model to classify the motor imagery type. When the feature vector corresponding to the first sample EEG signal and the feature vector corresponding to the second sample EEG signal are inputted into the domain discriminator, and the model is trained through the loss function, because the second sample EEG signal is EEG data generated when different human bodies corresponding to the first sample EEG signal perform motor imagery, the trained model has a good recognition degree for EEG signals triggered by different human bodies, which improves generalization capability of the trained model for the EEG recognition.

In an example embodiment, in a training process, the EEG signal classification model may analyze the feature vector corresponding to the first sample EEG signal and the feature vector corresponding to the second sample EEG signal through the domain discriminator, and update the EEG signal classification model according to the loss function. In an application process of the EEG signal classification model, the domain discriminator may be removed, and the classifier (e.g., the first fully connected layer) may be reserved, to classify the inputted EEG signals.

In an example embodiment, the EEG signal classification model further includes a dropout layer. The dropout layer is used for discarding a specified proportion of image features. The dropout layer may be located at various positions in the EEG signal classification model, and a probability of over-fitting of the model in a training process may be reduced by adding the dropout layer in the EEG signal classification model.

Operation 407. Obtain a first EEG signal.

In an example embodiment, at least two electrode signals of the first EEG signal may be EEG signals obtained by a signal processing device (such as a terminal device) through an electrode of the BCI and generated by the target object at the head. A quantity of the electrode signals is the same as a quantity of electrodes corresponding to the BCI. That is, the BCI may simultaneously obtain EEG signals generated by a same target object in different spatial regions of its head through different electrodes.

The first EEG signal may be an EEG signal obtained by the BCI through the electrode when the target object is performing motor imagery, or the first EEG signal may further be an EEG signal obtained by the BCI through the electrode when the target object is in a state out of the motor imagery.

In an example embodiment, the BCI obtains EEG signals generated in different regions of the head of the target object through electrodes connected to the target object, and the electrodes connected to the target object transmit EEG signals corresponding to each electrode to a terminal device corresponding to the BCI through different EEG channels.

In an example embodiment, the terminal device may obtain an original EEG signal generated by the target object based on each electrode of the BCI, and obtain the first sample EEG signal by performing filtering processing through a band-pass filter based on the original EEG signal.

Similar to processing operations of the original sample EEG signal, because there are many noises in the original EEG signal obtained through the electrode of the BCI, it is necessary to filter the original sample EEG signal through the band-pass filter, to reduce an influence of irrelevant noises on the EEG signal.

Operation 408. Obtain time-frequency feature maps respectively corresponding to the at least two electrode signals.

In an example embodiment, the signal processing device may respectively perform a normalization operation on the at least two electrode signals of the first sample EEG signal to obtain at least two standard signals, and obtain time-frequency feature maps respectively corresponding to the at least two electrode signals based on the at least two standard signals.

In an example embodiment, the signal processing device performs the CWT based on at least two electrode signals to obtain time-frequency feature maps respectively corresponding to at least two electrode signals.

In an example embodiment, the signal processing device obtains the time-frequency feature map corresponding to the first EEG signal based on the time-frequency feature maps respectively corresponding to the at least two electrode signals.

The first EEG signal includes at least two electrode signals, that is, the first EEG signal includes EEG signals generated in at least two regions of a head of the target object during motor imagery obtained by the BCI through at least two electrodes. In this case, the CWT is respectively performed on the at least two electrode signals, to obtain the time-frequency feature maps respectively corresponding to the at least two electrode signals, and then the time-frequency feature maps respectively corresponding to the at least two electrode signals are spliced according to a channel, to obtain the time-frequency feature map corresponding to the first EEG signal.

The time-frequency feature map corresponding to the first EEG signal includes image features of at least two channels, and the image features of the at least two channels respectively correspond to the time-frequency feature maps corresponding to at least two electrode signals.

Execution procedures of operation 406 and operation 407 may be similar to those of operation 401 and operation 402. This is not repeated herein.

Operation 409. Perform feature extraction on the time-frequency feature maps respectively corresponding to the at least two electrode signals through a first convolutional layer in an EEG signal classification model, to obtain the first extracted feature map.

The time-frequency feature map corresponding to the first EEG signal may be inputted to the first convolutional layer of the EEG signal classification model for feature extraction, to output the first extracted feature map.

In an example embodiment, image features of each channel in the first extracted feature map include image features of each channel in the time-frequency feature map corresponding to the first EEG signal.

For example, when the first convolutional layer is a 3*3 convolutional kernel, and a quantity of the convolutional kernels is 5, each convolutional kernel in the first convolutional layer is summed after performing a convolution operation with each channel in the time-frequency feature map corresponding to the first EEG signal, to obtain an image feature corresponding to the convolutional kernel. Therefore, when the five convolutional kernels respectively perform the convolution operation with the time-frequency feature map corresponding to each electrode signal in the time-frequency feature map corresponding to the first EEG signal, image features with five channels may be obtained, that is, a first extracted feature map whose quantity of channels is 5. In addition, because image features in each channel in the first extracted feature map are summed according to the convolution operation of each channel, the image features in each channel include image features of each channel (e.g., each electrode signal) in the time-frequency feature map corresponding to the first EEG signal. That is, feature extraction is performed on the time-frequency feature map corresponding to the first EEG signal through the first convolutional layer, and time-frequency features of each channel in the time-frequency feature map corresponding to the first EEG signal are fused. In addition, each channel in the first time-frequency feature map is an EEG signal of an object acquired by electrodes at different spatial positions, so that the fused first extracted feature map is a feature map having a time-domain feature, a frequency-domain feature, and a spatial-domain feature at the same time.

Operation 410. Perform, based on the attention weighted network in the EEG signal classification model, weighting processing based on the attention mechanism on features at different levels of the first extracted feature map, to obtain the attention feature map corresponding to the first EEG signal.

In an example embodiment, the features at different levels in the first extracted feature map are used for indicating features obtained after feature extraction through different convolutional layers in the first extracted feature map.

In an example embodiment, the first attention weighted network includes a first spatial attention weighted network, a second convolutional layer, a first channel attention network, and a third convolutional layer. The signal processing device may perform, based on the first spatial attention weighted network, weighting processing based on the spatial attention mechanism on the first extracted feature map to obtain a first spatial feature map; perform feature extraction on the first spatial feature map based on the second convolutional layer to obtain a second extracted feature map; perform, based on the first channel attention weighted network, weighting processing based on the channel attention mechanism on the second extracted feature map to obtain a first channel feature map; perform feature extraction on the first channel feature map based on the third convolutional layer to obtain a third extracted feature map; and obtain the attention feature map corresponding to the first EEG signal based on the first spatial feature map, the first channel feature map, and the third extracted feature map.

In an example embodiment, the first attention weighted network further includes the second attention weighted network. The first spatial feature map, the first channel feature map, and the third extracted feature map are fused to obtain a first fused feature map. Based on the first fused feature map, weight processing based on the attention mechanism is performed through the second attention weighted network, to obtain the attention feature map corresponding to the first EEG signal.

In an example embodiment, the second attention weighted network includes at least one of the second spatial attention weighted network and the second channel attention weighted network.

In an example embodiment, in a case that the second attention weighted network includes the second spatial attention weighted network and the second channel attention weighted network, the signal processing device may perform weighting processing based on the channel attention mechanism on the first fused feature map through the second channel attention weighted network, to obtain the second channel feature map, and perform weighting processing based on the spatial attention mechanism on the second channel feature map through the second spatial attention weighted network, to obtain the attention feature map corresponding to the first EEG signal.

Execution methods of operation 409 and operation 410 may be similar to those of a training process shown in operation 403 and operation 404. Details are not repeated herein.

Operation 411. Obtain a motor imagery type of the first EEG signal based on the attention feature map of the first EEG signal.

In an example embodiment, the signal processing device may obtain probability distribution corresponding to the first EEG signal based on the attention feature map of the first EEG signal, and the probability distribution being used for indicating probabilities that the first EEG signal is of each of various motor imagery types respectively; and obtain a motor imagery type of the first EEG signal based on the probability distribution of the first EEG signal.

In an example embodiment, the signal processing device may obtain a feature vector corresponding to the first EEG signal based on the attention feature map corresponding to the first EEG signal, and obtain probability distribution corresponding to the first EEG signal based on the feature vector corresponding to the first EEG signal.

In an example embodiment, the EEG signal classification model further includes a first fully connected layer. The signal processing device may perform data processing through the first fully connected layer based on the attention feature map corresponding to the first EEG signal to obtain the feature vector corresponding to the first EEG signal.

The signal processing device may input the attention feature map corresponding to the first EEG signal to the first fully connected layer, to obtain the feature vector corresponding to the first EEG signal. Sizes of values of different dimensions in the feature vector indicate possibility that the first EEG signal corresponds to different motor imagery types.

In an example embodiment, the signal processing device may input the feature vector corresponding to the first EEG signal to a softmax activation layer of the EEG signal classification model, to obtain the probability distribution corresponding to the first EEG signal.

In an example embodiment, the signal processing device may obtain a motor imagery type with a highest probability in the probability distribution corresponding to the first EEG signal as a motor imagery type corresponding to the first EEG signal.

In an example embodiment, when a probability of the motor imagery type with the highest probability in the probability distribution corresponding to the first EEG signal is greater than a threshold, the signal processing device may obtain the motor imagery type with the highest probability as the motor imagery type corresponding to the first EEG signal.

In another example embodiment, the signal processing device may determine the first EEG signal as an unrecognizable EEG signal when the probability corresponding to the motor imagery type with the highest probability in the probability distribution corresponding to the first EEG signal does not exceed the threshold.

Figure 9:
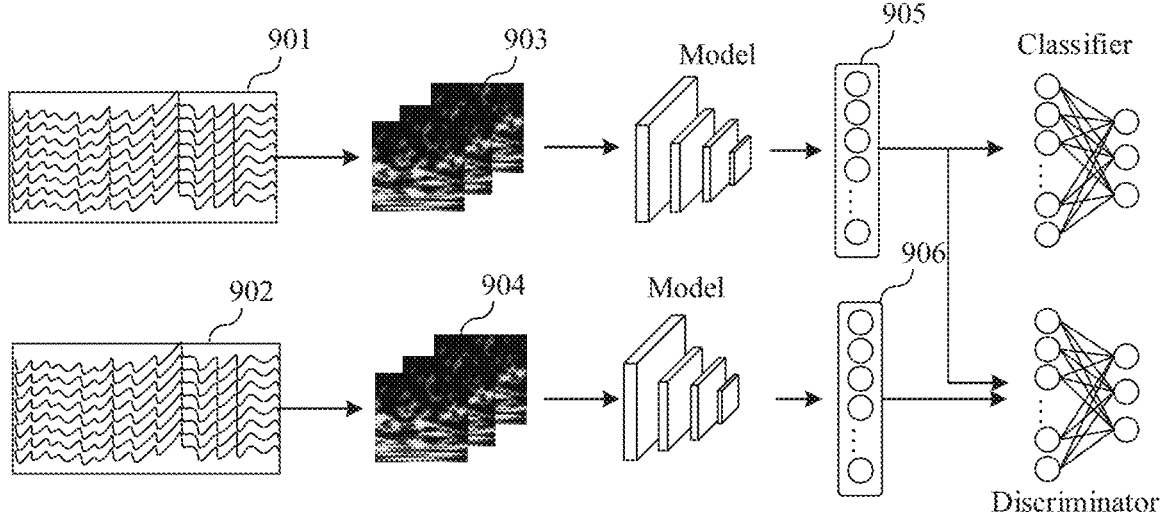
FIG. 9 is a schematic diagram of a principle of an EEG signal classification model used in the embodiment of FIG. 4.

FIG. 9 is a schematic diagram of a principle of an EEG signal classification model used in the embodiments of the disclosure. As shown in FIG. 9, in a training process of the EEG signal classification model, source domain data 901 (e.g., the first sample EEG signal) and target domain data 902 (e.g., the second sample EEG signal) may be inputted. A data preprocessing process (the wavelet transform) is performed on the source domain data to obtain source time-frequency data 903, the data preprocessing process is performed on the target domain data to obtain target time-frequency data 904, and the source time-frequency data and the target time-frequency data are respectively inputted into a model for feature extraction, to obtain a source feature vector 905 and a target feature vector 906. In this case, the source feature vector 905 is inputted to a classifier 910 for classification to obtain probability distribution corresponding to the source domain data. After the source feature vector 905 and the target feature vector 906 obtain a loss function value according to a domain adaptive mechanism, the model training device may update the model according to the loss function value. After the model is trained to converge, the acquired EEG signal belongs to the model, and a motor imagery type outputted by the model may be obtained.

The MI-BCI system has a wide application prospect in many fields, through which an external device may be controlled through imagining limb movements in the brain without any actual limb movements. The system may not only help a patient with physical inconvenience such as stroke hemiplegia to recover, or control a wheelchair to travel, but also be used for education and entertainment of an ordinary user, such as a brain-controlled VR game. Classification and recognition for an MI signal is a key process in the MI-BCI system, and its accuracy of decoding directly affects performance and user experience of this system. Because there are great differences in EEG signals of different subjects, in the related art, it is necessary to separately train a model for each subject, and carefully adjust a hyperparameter of the model, resulting in a time-consuming and tedious training process and poor classification performance. These problems limit application scenarios of a BCI interactive technology. In order to meet a requirement for performance and structure universality of EEG signal classification, in the solutions of the embodiments of the disclosure, an input signal is transformed to be represented by multi-domains and the input signal is processed through an attention adaptive model. A spatiotemporal feature of an EEG signal sequence is automatically extracted through deep learning, and an extracted EEG spatiotemporal feature has time invariance by using domain adaptation, which reduces differences between EEG signals of different subjects, solves a problem in the related art that each model of the subject needs to be separately fine-tuned and calibrated before applied due to individual differences, and effectively improves accuracy of MI classification.

According to the embodiments of the disclosure, for a temporal difference of a motor imagery EEG signal, an attention adaptive EEG signal classification model based on multi-domain representation is provided. First, each EEG signal sample is processed by band-pass filtering processing of 3 to 38 Hz to remove an influence caused by an irrelevant physiological noise such as an eye movement and a power frequency interference on the EEG signal. Then, signal disturbance of the filtered signal caused by the noise is reduced through an exponentially weighted moving average operation. Next, CWT is performed on each channel to obtain channel time-frequency representation, and time-frequency representations of all channels are spliced as input of an attention adaptive EEG decoding model. Key time-domain and spatial-domain features are automatically learned through the attention mechanism, and distribution of EEG data in a source domain and a target domain is aligned, so that the extracted EEG features are time invariant and a generalization capability for decoding a model is improved. Finally, the model predicts a motor imagery category corresponding to the inputted EEG signal. According to the solutions shown in the embodiments of the disclosure, an attention adaptive EEG decoding model based on multi-domain representations such as the spatial domain, the time domain, and the frequency domain is provided. Spatiotemporal features having identification and individual invariance may be extracted from EEG data of a plurality of subjects, which effectively improves decoding capability and accuracy of the model. According to the solutions shown in the embodiments of the disclosure, an attention mechanism and a domain adaptive mechanism are further introduced, through which the attention feature map may be generated according to an inputted sample, key channel, time information, and frequency information related to a classification task are located, so that a feature extractor may extract more separable features. In addition, by aligning conditional distribution of source domain data and target domain data, the generalization capability of the model in the target domain is enhanced, and the model performance is improved.

The technical solutions may be embedded into different hardware systems or software systems to achieve idea transmission and control for the subject. For example, a BCI system combined with an exoskeleton robot and the technical solution may be used for active rehabilitation of a motor function of a patient with hemiplegia or stroke. A BCI system combined with electric wheelchair may help a user with reduced mobility to travel freely. A brain-controlled VR game system combined with a game may implement that a human may control an activity of an object in a virtual world through mental imagination.

Because in this solution, importance of the channel and the time-frequency feature in the EEG signal are fully considered, and a network model is trained by using data of another subject, an available model for classification may be trained in a case that there is no label in target subject data, which may reduce acquisition time of labeled data and calibration time of the model, save manpower and material resources, improve identification capability and training efficiency of the MI-BCI system, and provide a better user experience.

In the technical solutions, a motor imagery open data set from open competition data, the BCI Competition IV Dataset 2a, is used. This data set includes 9 subjects, in which EEG data of each subject is recorded by 22 EEG electrodes and 3 electrooculogram electrodes, and a signal sampling rate is 250 Hz, including 4 types of motor imagery (left hand, right hand, feet, and tongue). The experiment includes two stages. In this technology, a data file acquired in a training stage of each subject is used as a training set and a data file acquired in a testing stage is used as a testing set.

In this solution, a signal of a motor imagery interval is intercepted for each sample, that is, data of 4 s from 2 s to 6 s. Because a signal sampling frequency is 250 Hz, a time dimension of each sample is 1000. In this solution, 3 electrooculogram channels are directly removed, and only 22 EEG channels related to a motor imagery task are considered. A third-order Butterworth filter is selected for band-pass filtering, and a band-pass range is from 3 to 38 Hz. Signal normalization uses an exponentially weighted moving average method, and a weight parameter is set to 0.999, or other normalization operations may be used, such as mean variance normalization, or a CSP algorithm.

In this solution, spatial-temporal and frequency domain representation of EEG is obtained from the original EEG signal by using the CWT. First, the CWT is performed on a signal of each EEG channel, and time-frequency feature maps corresponding to all EEG channels are spliced to form a multi-domain representation fusing spatial information, time information, and frequency domain information. In this solution, 'cmor3.0-3.0' is used as a wavelet basis function, and resolution is set to 256. Other wavelet basis functions, such as haar wavelet, db wavelet, sym wavelet and coif series wavelet may also be selected herein.

Figure 10:
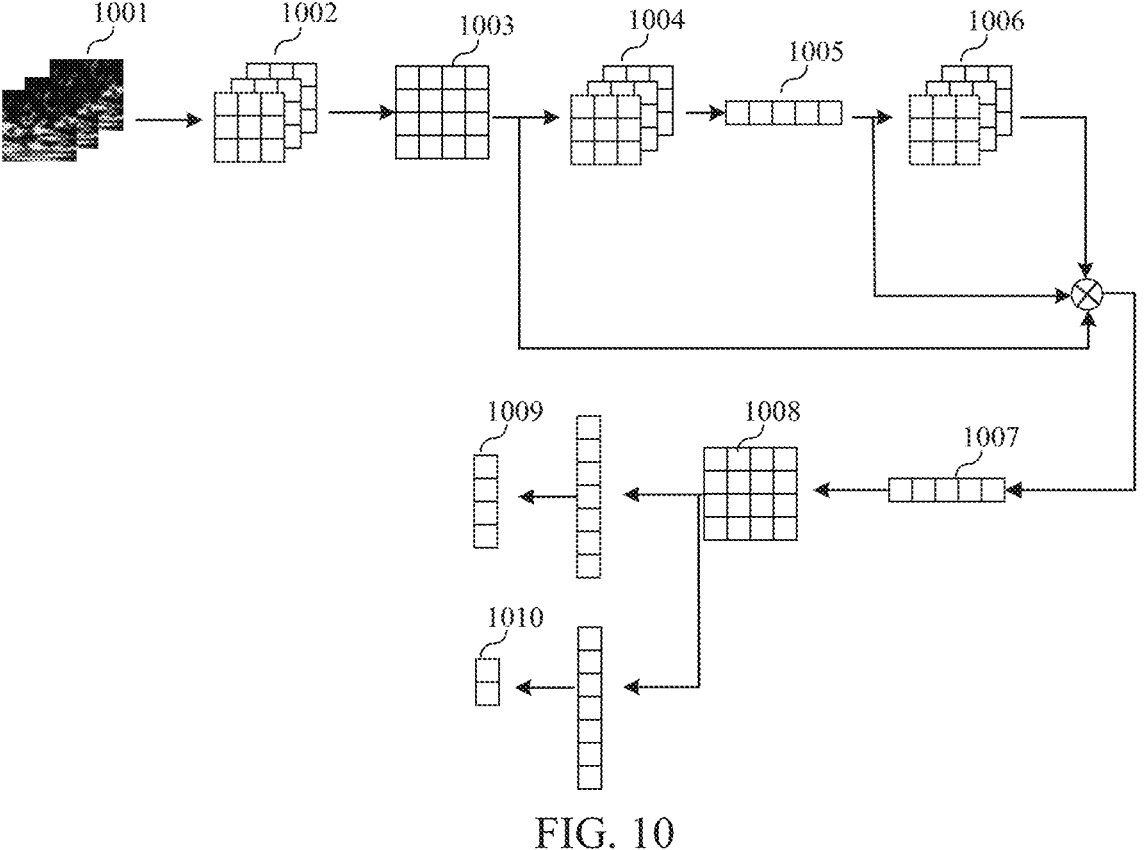
FIG. 10 is a schematic diagram of application of an EEG signal classification model used in the embodiment of FIG. 4.

FIG. 10 is a schematic diagram of application of an EEG signal classification model used in the embodiments of the disclosure. As shown in FIG. 10, in the embodiments of the disclosure, an attention adaptive EEG signal classification model based on multi-domain representation is designed according to a time feature, a spatial feature, and a frequency feature of an inputted EEG signal, and its basic model parameters are shown in Table 1. The decoding model includes three parts: a feature extractor, a classifier, and a domain discriminator. A signal 1001 inputted to a network includes a source domain signal (e.g., the first sample EEG signal) and a target domain signal (e.g., the second sample EEG signal), and a size of each signal is N×61×160 (N is a quantity of electrodes). A first layer of the feature extractor is a convolutional layer 'Conv_1-Batch Normalization-ReLu' (e.g., a first convolutional layer 1002), in which a size of a convolutional kernel is 3×15, a stride is 1, and a quantity of convolutional channels is 8. A second layer is a spatial attention layer 'Spatial Attention' (e.g., a first spatial attention weighted network 1003), in which a spatial attention map is generated according to an input signal, a size of a convolutional kernel is 3×3, a stride is 1, and a quantity of convolutional channels is 1. A third layer is a convolutional layer 'Conv_2-Batch Normalization-ReLu' (e.g., a second convolutional layer 1004), in which a size of a convolutional kernel is 3×15, a stride is 1, and a quantity of convolutional channels is 16. Then, the feature map is compressed in size through an average pooling layer (whose core size is 2×2, and stride is 2×2), and each convolutional channel is weighted through channel attention 'Channel Attention' (e.g., a first channel attention weighted network 1005). A channel attention weight is generated by a fully connected layer with 4 hidden nodes, and then a dropout layer 'Dropout' is connected to, overfitting is suppressed, and a dropout rate is set to 0.5. A seventh layer is a convolutional layer 'Conv_3-Batch Normalization-ReLu' (e.g., a third convolutional layer 1006), in which a size of a convolutional kernel is 3×15, a stride is 1, and a quantity of convolutional channels is 32. After that, a size of the feature map is compressed through an average pooling layer (whose core size is 2×2, and stride is 2×2). In order to fuse information in different levels and enhance flow of network information, output of a first dropout layer and output of a first spatial attention layer form a 13×26 feature map through adaptive mean pooling, and the feature map is spliced with output of a third convolutional layer according to the convolutional channel. Each convolutional channel is weighted through the channel attention 'Channel Attention' (e.g., a second channel attention weighted network 1007), and the attention weight is generated by a fully connected layer with 8 hidden nodes. Then, a spatial attention map is generated through a spatial attention layer 'Spatial Attention' (e.g., a second spatial attention weighted network 1008), in which a size of a convolutional kernel is 3×3, a stride is 1, and a quantity of convolutional channels is 1.

Finally, the spatial attention map is flattened as a deep EEG feature, a spatial attention map of the first sample EEG signal is tiled as a feature vector corresponding to the first sample EEG signal, and a spatial attention map of the second sample EEG signal is tiled as a feature vector corresponding to the second sample EEG signal, which are respectively transmitted to a Classifier 1009 and a Domain Discriminator 1010. The classifier is responsible for completing a task of EEG signal classification, and the domain discriminator is responsible for determining whether the EEG signal belongs to a source domain signal or a target domain signal. According to both of them, a final classification probability is outputted through a fully connected layer and a Softmax activation layer in network structure design. In particular, the classifier outputs four types of prediction probabilities (corresponding to left hand, right hand, feet, and tongue), and the domain discriminator outputs two types of prediction probabilities (corresponding to the source domain and the target domain).

TABLE 1

Parameter table of attention adaptive EEG decoding model

| Parameter layer | Output size | Parameter |
| --- | --- | --- |
| Input | N*61*160 | — |
| Conv_1 | 8 × 59 × 146 | 3 × 15, 8, stride 1 |
| Batch Normalization | — | — |
| ReLu | — | — |
| Spatial Attention | 8 × 59 × 146 | 3 × 3 |
| Conv_2 | 16 × 57 × 132 | 3 × 15, 16, stride 1 |
| Batch Normalization | 16 × 57 × 132 | — |
| ReLu | 16 × 57 × 132 | — |
| Average pooling | 16 × 28 × 66 | 2 × 2 |
| Channel Attention | 16 × 28 × 66 | 4 hidden nodes |
| Dropout | 16 × 28 × 66 | p = 0.5 |
| Conv_3 | 32 × 26 × 52 | 3 × 15, 32, stride 1 |
| Batch Normalization | 32 × 26 × 52 | — |
| ReLu | 32 × 26 × 52 | — |
| Average pooling | 32 × 13 × 26 | 2 × 2 |
| Channel Attention | 32 × 13 × 26 | 8 hidden nodes |
| Spatial Attention | 32 × 13 × 26 | 3 × 3 |
| FC_1 | C | C output nodes |
| FC_2 | 2 | 2 output nodes |

In the embodiments of the disclosure, a parameter of a neural network model may be solved by using an Adam-based gradient descent method, and a model parameter may be initialized by using a Xavier initialization method. In a solving process, an EEG multi-domain representation and a corresponding tag of each subject are transmitted to a network for learning, and the model is optimized through error backpropagation.

In the solutions shown in the embodiments of the disclosure, classification of end-to-end decoding is performed on motor imagery spatial-time-frequency domain representations through a deep learning technology, and a tedious feature extraction process through the prior knowledge is unnecessary, so that the model is more universal. A multi-domain feature map is formed by using the spatial information, time information, and frequency information of the EEG signal, so that an EEG feature related to the task may be completely retained. By introducing the attention mechanism to learn the EEG feature map, the network may be guided to pay more attention to features of specific channel, frequency, and time through supervised training, which makes model learning more separable. An adversarial learning mechanism is introduced to force the feature extractor to extract an EEG feature that is common to all subjects from the EEG feature map, so that the deep model has better generalization capability.

According to the solutions shown in the embodiments of the disclosure, the time-frequency feature map is a time-frequency feature map corresponding to EEG signals generated by the target object in regions corresponding to different electrode signals. That is, the time-frequency feature map further includes a spatial relationship between different electrode signals. Therefore, feature extraction is performed on the time-frequency feature map through the trained EEG signal classification model, through which the time-domain feature and frequency-domain feature of the EEG signal may be considered at the same time. The feature map extracted from the time-frequency feature map is weighted through the attention mechanism, through which a spatial relationship between at least two electrode signals of the EEG signal may be considered. Therefore, the attention feature map finally obtained is a feature extracted by fusing a time-domain feature, a frequency-domain feature, and a spatial-domain feature of the EEG signal at the same time. On a basis of ensuring diversification of image feature levels, positions of rich features in the feature map may be paid more attention through the attention mechanism. Therefore, accuracy of predicting the motor imagery type of the EEG signal may be improved by determining the motor imagery type corresponding to the first EEG signal through the attention feature map.

Figure 11:
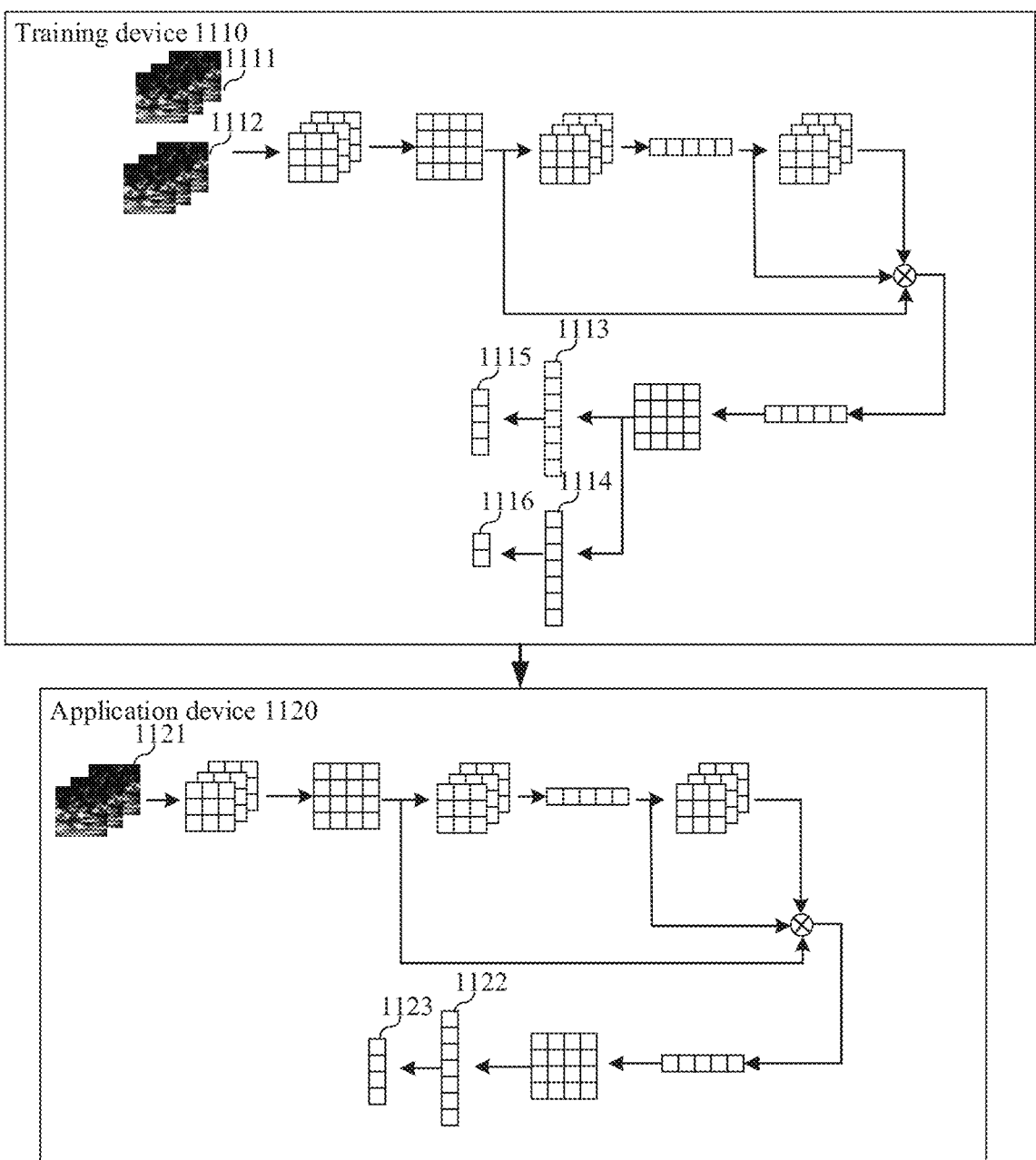
FIG. 11 is a flowchart of model training and model application according to an example embodiment.

FIG. 11 is a flowchart of model training and model application according to an example embodiment. The model training and model application process may be jointly executed by a model training device 1100 and a model application device (e.g., the signal processing device) 1110. As shown in FIG. 11, the model training and model application process is as follows:

In the training device 1110, source domain data (the time-frequency feature map corresponding to the first sample EEG signal) 1111 and target domain data 1112 (the time-frequency feature map corresponding to the second sample EEG signal) are respectively inputted into the EEG signal classification model. The EEG signal classification model in the embodiments of the disclosure may be the EEG signal classification model shown in FIG. 10 and details of a specific structure thereof are not described herein. After the time-frequency feature map 1111 corresponding to the first sample EEG signal is processed through the EEG signal classification model, an obtained feature map corresponding to the first sample EEG signal may be inputted to a first fully connected layer 1113 in the EEG signal classification model, to obtain probability distribution 1115 corresponding to the first sample EEG signal. According to the probability distribution corresponding to the first sample EEG signal and a motor imagery type corresponding to the first sample EEG signal, a first loss function value may be obtained.

In the training device 1110, after a time-frequency feature map 1112 corresponding to the second sample EEG signal is processed through the EEG signal classification model, an obtained feature map corresponding to the second sample EEG signal and the feature map corresponding to the first sample EEG signal may be inputted into a discriminator 1114 in the EEG signal classification model, to respectively obtain a domain classification probability corresponding to the first sample EEG signal and a domain classification probability corresponding to the second sample EEG signal. The domain classification probabilities are used for indicating probabilities that the first sample EEG signal and the second sample EEG signal belong to a training set corresponding to the first sample EEG signal. A second loss function value may be obtained according to the domain classification probability corresponding to the first sample EEG signal and the domain classification probability corresponding to the second sample EEG signal.

In the training device 1110, the EEG signal classification model may perform parameter update according to the first loss function value and the second loss function value, and the first loss function value may ensure a motor imagery classification capability of the updated EEG signal classification model for the EEG signal. The second loss function value may make the model have certain recognition capability for the second EEG signal sample, and improve generalization of the trained model.

After the EEG signal classification model is trained, the EEG signal classification model may be transmitted to an application device 1120. In the embodiments of the disclosure, because the domain discriminator increases the generalization of the model based on a transfer learning mechanism, the EEG signal classification model may discard the domain discriminator. That is, the application device 1120 may only load part of the EEG signal classification model, so as to perform feature extraction on an inputted first EEG signal 1121 to obtain an extracted feature map, and input the extracted feature map into a first fully connected layer 1122 in the application device to obtain probability distribution 1123 corresponding to the first EEG signal.

Figure 12:
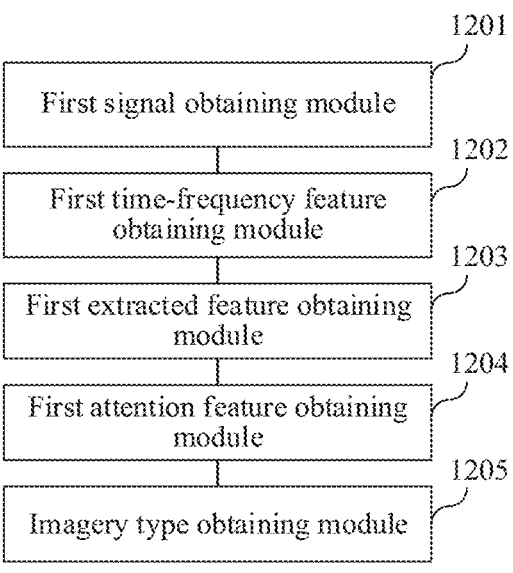
FIG. 12 is a structural block diagram of an EEG signal classification apparatus according to an example embodiment.

FIG. 12 is a structural block diagram of an EEG signal classification apparatus according to an example embodiment. The EEG signal classification apparatus may implement all or part of operations in the method provided in the embodiments shown in FIG. 2 or FIG. 4. The EEG signal classification apparatus includes:

a first signal obtaining module 1201, configured to obtain a first EEG signal, the first EEG signal including at least two electrode signals, and the electrode signal being used for indicating an EEG signal generated by a target object in a spatial region of the electrode signal;

a first time-frequency feature obtaining module 1202, configured to obtain time-frequency feature maps of the at least two electrode signals, the time-frequency feature map being used for indicating a time-domain feature and a frequency-domain feature of the electrode signal;

a first extracted feature obtaining module 1203, configured to perform feature extraction based on the time-frequency feature maps of the at least two electrode signals to obtain a first extracted feature map, the first extracted feature map being fused with spatial features of the at least two electrode signals, and the spatial features of the at least two electrode signals being related to spatial regions of the at least two electrode signals;

a first attention feature obtaining module 1204, configured to perform weighting processing based on an attention mechanism on the first extracted feature map to obtain an attention feature map of the first EEG signal; and an imagery type obtaining module 1205, configured to obtain a motor imagery type of the first EEG signal based on the attention feature map corresponding to the first EEG signal.

In an example embodiment, the first extracted feature obtaining module 1203 includes:

a first extracted feature map obtaining unit, configured to perform feature extraction on the time-frequency feature maps of the at least two electrode signals through a first convolutional layer in an EEG signal classification model, to obtain the first extracted feature map; and the first attention feature obtaining module 1203 includes:

an attention feature obtaining unit, configured to perform, based on a first attention weighted network in the EEG signal classification model, weighting processing based on the attention mechanism on the first extracted feature map to obtain the attention feature map corresponding to the first EEG signal, the EEG signal classification model being a machine learning model trained by using a first sample EEG signal as a sample and a motor imagery type corresponding to the first sample EEG signal as a label.

In an example embodiment, the attention mechanism includes at least one of a spatial attention mechanism and a channel attention mechanism.

In an example embodiment, the first attention weighted network includes a first spatial attention weighted network, a second convolutional layer, a first channel attention network, and a third convolutional layer.

The attention feature obtaining unit includes:

a first spatial weighted subunit, configured to perform, based on the first spatial attention weighted network, weighting processing based on the spatial attention mechanism on the first extracted feature map to obtain a first spatial feature map;

a second feature obtaining subunit, configured to perform feature extraction on the first spatial feature map based on the second convolutional layer to obtain a second extracted feature map;

a first channel weighted subunit, configured to perform, based on the first channel attention weighted network, weighting processing based on the channel attention mechanism on the second extracted feature map to obtain a first channel feature map;

a third feature obtaining subunit, configured to perform feature extraction on the first channel feature map based on the third convolutional layer to obtain a third extracted feature map; and an attention feature obtaining subunit, configured to obtain the attention feature map based on the first spatial feature map, the first channel feature map, and the third extracted feature map.

In an example embodiment, the first attention weighted network further includes the second attention weighted network.

The attention feature obtaining subunit further includes:

a first fusion subunit, configured to fuse the first spatial feature map, the first channel feature map, and the third extracted feature map to obtain a first fused feature map; and a first attention weighted subunit, configured to perform, through the second attention weighted network, weighting processing based on the attention mechanism on the first fused feature map to obtain the attention feature map.

In an example embodiment, in a case that the second attention weighted network includes a second spatial attention weighted network and a second channel attention weighted network, the first attention weighted subunit further includes:

a second channel attention weighted subunit, configured to perform, through the second channel attention weighted network, weighting processing based on the channel attention mechanism on the first fused feature map to obtain a second channel feature map; and a second spatial attention weighted subunit, configured to perform, through the second spatial attention weighted network, weighting processing based on the spatial attention mechanism on the second channel feature map to obtain the attention feature map.

In an example embodiment, the first time-frequency feature obtaining module 1202 includes:

an electrode time-frequency signal obtaining unit, configured to perform continuous wavelet transform based on the at least two electrode signals to obtain the time-frequency feature maps of the at least two electrode signals.

In an example embodiment, the EEG signal classification model further includes a first fully connected layer.

The imagery type obtaining module 1205 is further configured to perform, through the first fully connected layer, data processing on the attention feature map of the first EEG signal to obtain a feature vector of the first EEG signal;

obtain probability distribution of the first EEG signal based on the feature vector corresponding to the first EEG signal, the probability distribution being used for indicating probabilities that the first EEG signal is of each of various motor imagery types respectively; and determine a motor imagery type of the first EEG signal based on the probability distribution of the first EEG signal.

According to the solutions shown in the embodiments of the disclosure, the time-frequency feature map is a time-frequency feature map corresponding to EEG signals generated by the target object in regions corresponding to different electrode signals. That is, the time-frequency feature map further includes a spatial relationship between different electrode signals. Therefore, feature extraction is performed on the time-frequency feature map through the EEG signal classification model, through which the time-domain feature and frequency-domain feature of the EEG signal may be considered at the same time. The feature map extracted from the time-frequency feature map is weighted through the attention mechanism, through which a spatial relationship between at least two electrode signals of the EEG signal may be considered. Therefore, the attention feature map finally obtained is a feature extracted by fusing a time-domain feature, a frequency-domain feature, and a spatial-domain feature of the EEG signal at the same time. On a basis of ensuring diversification of image feature levels, positions of rich features in the feature map may be paid more attention through the attention mechanism. Therefore, accuracy of predicting the motor imagery type of the EEG signal may be improved by determining the motor imagery type corresponding to the first EEG signal through the attention feature map.

Figure 13:
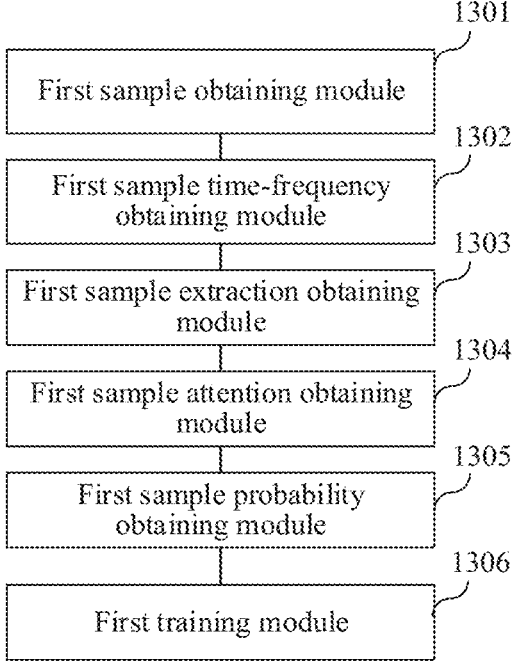
FIG. 13 is a structural block diagram of an EEG signal classification apparatus according to an example embodiment.

FIG. 13 is a structural block diagram of an EEG signal classification apparatus according to an example embodiment. The EEG signal classification apparatus may implement all or part of operations in the method provided in the embodiments shown in FIG. 3 or FIG. 4. The EEG signal classification apparatus includes:

a first sample obtaining module 1301, configured to obtain a first sample EEG signal, the first sample EEG signal including at least two first sample electrode signals, and the first sample electrode signal being used for indicating an EEG signal generated in a spatial region of the first sample electrode signal in a case that a target object performs motor imagery;

a first sample time-frequency obtaining module 1302, configured to obtain first sample time-frequency feature maps of the at least two first sample electrode signals, the first sample time-frequency feature map being used for indicating a time-domain feature and a frequency-domain feature of the first sample electrode signal;

a first sample extraction obtaining module 1303, configured to perform feature extraction on the first sample time-frequency feature maps of the at least two first sample electrode signals through a first convolutional layer in an EEG signal classification model, to obtain a first sample extracted feature map, the first sample extracted feature map being fused with spatial features of the at least two first sample electrode signals, and the spatial features of the at least two first sample electrode signals being related to spatial regions of the at least two first sample electrode signals;

a first sample attention obtaining module 1304, configured to perform, based on an attention weighted network in the EEG signal classification model, weighting processing based on the attention mechanism on the first sample extracted feature map to obtain the attention feature map of the first sample EEG signal;

a first sample probability obtaining module 1305, configured to obtain sample probability distribution of the first sample EEG signal based on the attention feature map corresponding to the first sample EEG signal, the sample probability distribution being used for indicating probabilities that the first sample EEG signal is of each of various motor imagery types respectively; and a first training module 1306, configured to train the EEG signal classification model based on the sample probability distribution and the motor imagery type of the first sample EEG signal.

The EEG signal classification model is used for predicting the motor imagery type of the first EEG signal based on the first EEG signal.

In an example embodiment, the apparatus further includes:

a second EEG signal obtaining module, configured to obtain a second sample EEG signal; the second sample EEG signal including at least two second sample electrode signals, and the second sample electrode signal being used for indicating an EEG signal generated in a spatial region of the second sample electrode signal in a case that a target object performs motor imagery;

a second sample time-frequency feature map obtaining module, configured to obtain second sample time-frequency feature maps of the at least two second sample electrode signals, the second sample time-frequency feature map being used for indicating a time-domain feature and a frequency-domain feature corresponding to the second sample electrode signal;

a second sample extracted feature map obtaining module, configured to perform feature extraction on the second sample time-frequency feature maps of the at least two second sample electrode signals through a first convolutional layer in an EEG signal classification model, to obtain a second sample extracted feature map, the second sample extracted feature map being fused with spatial features of the at least two second sample electrode signals, and the spatial features of the at least two second sample electrode signals being related to spatial regions of the at least two second sample electrode signals; and a second attention feature obtaining module, configured to perform, based on an attention weighted network in the EEG signal classification model, weighting processing based on the attention mechanism on the second sample extracted feature map to obtain the attention feature map of the second sample EEG signal.

The first model training module is further configured to:

train the EEG signal classification model based on the sample probability distribution, the motor imagery type of the first sample EEG signal, the attention feature map corresponding to the first sample EEG signal, and the attention feature map corresponding to the second sample EEG signal.

In an example embodiment, the second sample EEG signal may indicate EEG signals generated by a target object corresponding to the first sample EEG signal at different moments, or the second sample EEG signal may indicate an EEG signal generated by a human body other than the target object corresponding to the first sample EEG signal.

According to the solutions shown in the embodiments of the disclosure, the time-frequency feature map is a time-frequency feature map corresponding to EEG signals generated by the target object in regions corresponding to different electrode signals. That is, the time-frequency feature map further includes a spatial relationship between different electrode signals. Therefore, feature extraction is performed on the time-frequency feature map through the EEG signal classification model, through which the time-domain feature and frequency-domain feature of the EEG signal may be considered at the same time. The feature map extracted from the time-frequency feature map is weighted through the attention mechanism, through which a spatial relationship between at least two electrode signals of the EEG signal may be considered. Therefore, the attention feature map finally obtained is a feature extracted by fusing a time-domain feature, a frequency-domain feature, and a spatial-domain feature of the EEG signal at the same time. On a basis of ensuring diversification of image feature levels, positions of rich features in the feature map may be paid more attention through the attention mechanism. Therefore, accuracy of predicting the motor imagery type of the EEG signal may be improved by determining the motor imagery type corresponding to the first EEG signal through the attention feature map.

Figure 14:
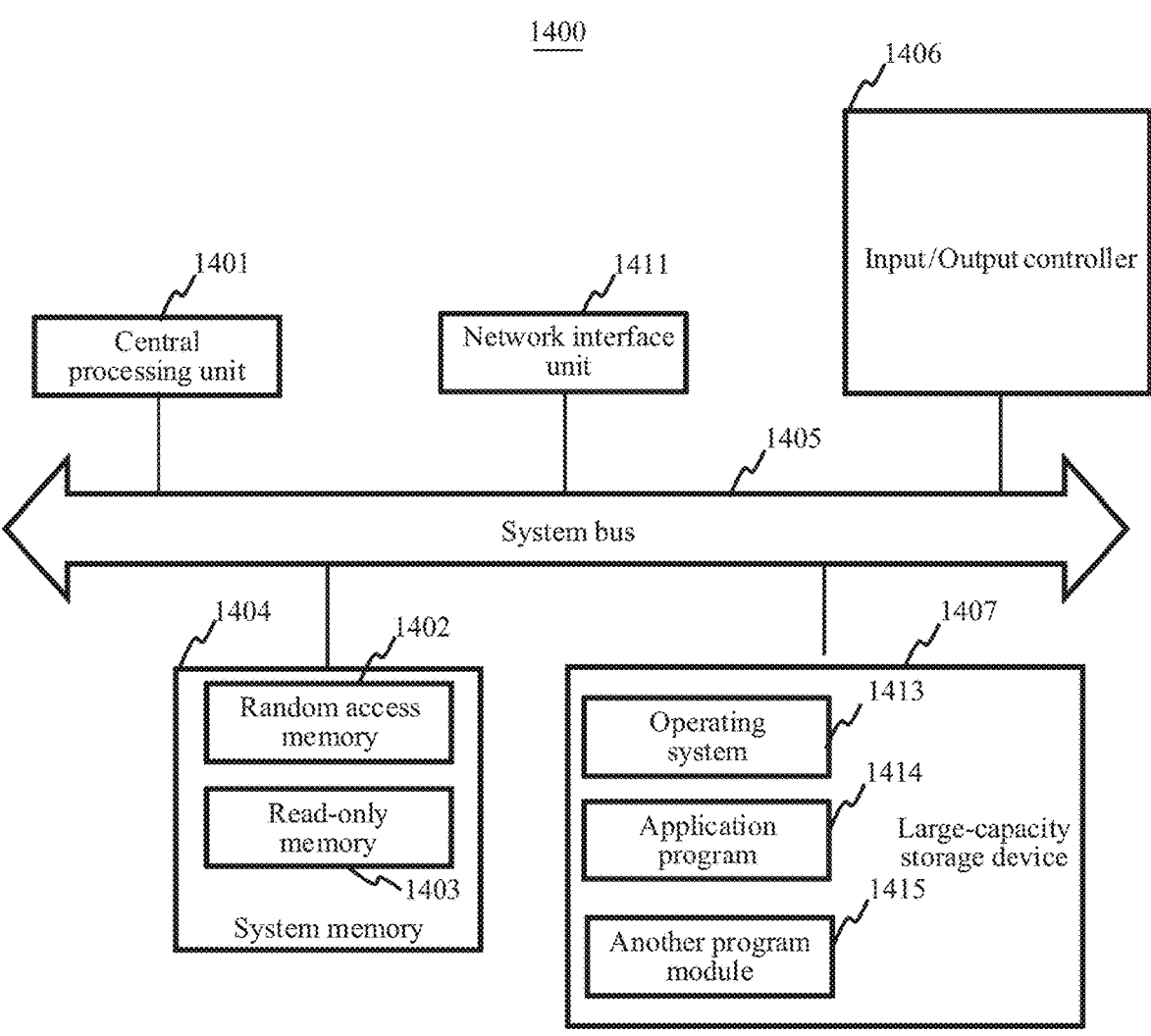
FIG. 14 is a schematic structural diagram of a computer device according to an example embodiment.

FIG. 14 is a schematic structural diagram of a computer device according to an example embodiment. The computer device may be implemented as the model training device and/or the signal processing device in the various method embodiments described above. The computer device 1400 includes a central processing unit (CPU) 1401, a system memory 1404 including a random access memory (RAM) 1402 and a read-only memory (ROM) 1403, and a system bus 1405 connecting the system memory 1404 to the CPU 1401. The computer device 1400 further includes a basic input/output system (I/O system) 1406 configured to transmit information between components in the computer, and a mass storage device 1407 configured to store an operating system 1413, an application program 1414, and another program module 1415.

The mass storage device 1407 is connected to the CPU 1401 through a mass storage controller (not shown) connected to the system bus 1405. The mass storage device 1407 and an associated computer-readable medium provide non-volatile storage for the computer device 1400. That is, the mass storage device 1407 may include a computer-readable medium (not shown) such as a hard disk or a compact disc ROM (CD-ROM) drive.

In general, the computer-readable medium may include a computer storage medium and a communication medium. The computer storage medium includes volatile and non-volatile, removable and non-removable media that store information such as computer-readable instructions, data structures, program modules, or other data and that are implemented by using any method or technology. The computer storage medium includes a RAM, a ROM, a flash memory, or other solid storage technologies; a CD-ROM, or other optical storages; and a cassette, a magnetic tape, a disk storage, or other magnetic storage devices. Certainly, those skilled in the art may learn that the computer storage medium is not limited to the above. The system memory 1404 and the mass storage device 1407 described above may be collectively referred to as memory.

The computer device 1400 may be connected to the Internet or another network device by using a network interface unit 1411 connected to the system bus 1405.

The memory further includes one or more computer instructions. The one or more computer instructions are stored in the memory. The CPU 1401 executes the one or more computer instructions to implement all or some of operations of the method shown in FIG. 2, FIG. 4, or FIG. 5.

In an example embodiment, a non-temporary computer-readable storage medium including an instruction, for example, a memory including a computer program (an instruction), is further provided, and the program (the instruction) may be executed by a processor of a computer device to complete the methods shown in the embodiments of the disclosure. For example, the non-temporary computer-readable storage medium may be a read-only memory (ROM), a random access memory (RAM), a compact disc ROM (CD-ROM), a magnetic tape, a floppy disk, an optical data storage device, or the like.

In an example embodiment, a computer program product or a computer program is further provided. The computer program product or the computer program includes computer instructions, and the computer instructions are stored in a computer-readable storage medium. A processor of a computer device reads the computer instructions from the computer-readable storage medium. The processor executes the computer instructions, to cause the computer device to perform the method shown in the foregoing embodiments.

Herein, the term "module" may indicate, but is not limited to, a software and/or hardware component, such as a field programmable gate array (FPGA) or an application specific integrated circuit (ASIC), which performs certain tasks. A module may be configured to reside in a tangible addressable storage medium and be configured to execute on one or more processors. For example, a "module" may include components such as software components, object-oriented software components, class components and task components, and processes, functions, routines, segments of program code, drivers, firmware, microcode, circuitry, data, databases, data structures, tables, arrays, and variables. A "module" may be divided into a plurality of "modules" that perform detailed functions.

At least one of the components, elements, modules or units (collectively "components" in this paragraph) represented by a block in the drawings may be embodied as various numbers of hardware, software and/or firmware structures that execute respective functions described above, according to an example embodiment. According to example embodiments, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

The foregoing is illustrative of example embodiments and is not to be construed as limiting thereof. Although some example embodiments have been described, those skilled in the art will readily appreciate that many modifications are possible in the example embodiments without materially departing from the novel teachings and advantages of the example embodiments. Accordingly, all such modifications are intended to be included within the scope of the example embodiments as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims and their equivalents.

The technical solutions provided in the embodiments of the disclosure achieve at least the following beneficial effects.

An EEG signal including at least two electrode signals is obtained, and a time-frequency feature map is obtained according to the at least two electrode signals. The time-frequency feature map may indicate a time-domain feature and a frequency-domain feature of the electrode signal. Then, feature extraction is performed on the time-frequency feature map to obtain a first extracted feature map, and features at different levels of the extracted first extracted feature map are weighted based on an attention mechanism, to obtain a weighted attention feature map. Finally a motor imagery type of the EEG signal is determined through the weighted attention feature map. In the foregoing solution, the time-frequency feature map is a time-frequency feature map of EEG signals generated by the target object in different electrode signal regions. That is, the time-frequency feature map further includes a spatial relationship between different electrode signals. Therefore, feature extraction is performed on the time-frequency feature map, through which the time-domain feature and frequency-domain feature of the EEG signal may be considered at the same time. The feature map extracted from the time-frequency feature map is weighted through the attention mechanism, through which a spatial relationship between at least two electrode signals of the EEG signal may be considered. Therefore, the attention feature map finally obtained is a feature extracted by fusing a time-domain feature, a frequency-domain feature, and a spatial-domain feature of the EEG signal at the same time. On a basis of ensuring diversification of image feature levels, positions of rich features in the feature map may be paid more attention through the attention mechanism. Therefore, accuracy of predicting the motor imagery type of the EEG signal may be improved by determining the motor imagery type of the first EEG signal through the attention feature map.

What is claimed is:

1. An electroencephalogram (EEG) signal classification method, performed by at least one processor, the method comprising:

obtaining a first EEG signal, the first EEG signal comprising at least two electrode signals, an electrode signal of the at least two electrode signals indicating an EEG signal generated by a target object in a spatial region corresponding to the electrode signal;

obtaining time-frequency feature maps of the at least two electrode signals, a time-frequency feature map indicating a time-domain feature and a frequency-domain feature of the electrode signal;

performing feature extraction based on the time-frequency feature maps of the at least two electrode signals through a first convolutional layer in an EEG signal classification model to obtain a first extracted feature map, the first extracted feature map being fused with spatial features of the at least two electrode signals, and the spatial features of the at least two electrode signals being related to spatial regions corresponding to the at least two electrode signals;

performing, based on a first attention weighted network in the EEG signal classification model, weighting processing based on an attention mechanism on the first extracted feature map to obtain an attention feature map of the first EEG signal; and obtaining a motor imagery type of the first EEG signal based on the attention feature map of the first EEG signal, wherein the EEG signal classification model is trained based on a motor imagery type corresponding to a first sample EEG signal and a sample probability distribution corresponding to the first sample EEG signal, the sample probability distribution indicating probabilities that the first sample EEG signal is of each of various motor imagery types, respectively.

2. The method according to claim 1, wherein the attention mechanism comprises at least one of a spatial attention mechanism or a channel attention mechanism.

3. The method according to claim 2, wherein the first attention weighted network comprises a first spatial attention weighted network, a second convolutional layer, a first channel attention weighted network, and a third convolutional layer; and the performing, based on the first attention weighted network in the EEG signal classification model, the weighting processing based on the attention mechanism on the first extracted feature map to obtain the attention feature map of the first EEG signal comprises:

performing, based on the first spatial attention weighted network, weighting processing based on the spatial attention mechanism on the first extracted feature map to obtain a first spatial feature map;

performing feature extraction on the first spatial feature map based on the second convolutional layer to obtain a second extracted feature map;

performing, based on the first channel attention weighted network, weighting processing based on the channel attention mechanism on the second extracted feature map to obtain a first channel feature map;

performing feature extraction on the first channel feature map based on the third convolutional layer to obtain a third extracted feature map; and obtaining the attention feature map based on the first spatial feature map, the first channel feature map, and the third extracted feature map.

4. The method according to claim 3, wherein the first attention weighted network further comprises a second attention weighted network; and the obtaining the attention feature map based on the first spatial feature map, the first channel feature map, and the third extracted feature map comprises:

fusing the first spatial feature map, the first channel feature map, and the third extracted feature map to obtain a first fused feature map; and performing, through the second attention weighted network, weighting processing based on the attention mechanism on the first fused feature map to obtain the attention feature map.

5. The method according to claim 4, wherein the second attention weighted network comprises a second spatial attention weighted network and a second channel attention weighted network; and the performing, through the second attention weighted network, the weighting processing based on the attention mechanism on the first fused feature map to obtain the attention feature map comprises:

performing, through the second channel attention weighted network, weighting processing based on the channel attention mechanism on the first fused feature map to obtain a second channel feature map; and performing, through the second spatial attention weighted network, weighting processing based on the spatial attention mechanism on the second channel feature map to obtain the attention feature map.

6. The method according to claim 1, wherein the obtaining the time-frequency feature maps of the at least two electrode signals comprises:

performing continuous wavelet transform based on the at least two electrode signals to obtain the time-frequency feature maps of the at least two electrode signals.

7. The method according to claim 6, wherein the EEG signal classification model further comprises a first fully connected layer; and the obtaining the motor imagery type of the first EEG signal based on the attention feature map of the first EEG signal comprises:

performing, through the first fully connected layer, data processing on the attention feature map of the first EEG signal to obtain a feature vector of the first EEG signal;

obtaining a probability distribution of the first EEG signal based on the feature vector of the first EEG signal, the probability distribution indicating probabilities that the first EEG signal is of each of a plurality of motor imagery types, respectively; and determining the motor imagery type of the first EEG signal based on the probability distribution of the first EEG signal.

8. An electroencephalogram (EEG) signal classification method, performed by at least one processor, the method comprising:

obtaining a first sample EEG signal, the first sample EEG signal comprising at least two first sample electrode signals, and a first sample electrode signal indicating an EEG signal generated in a spatial region corresponding to the first sample electrode signal from a target object that performs motor imagery;

obtaining first sample time-frequency feature maps of the at least two first sample electrode signals, a first sample time-frequency feature map indicating a time-domain feature and a frequency-domain feature of a corresponding first sample electrode signal;

performing feature extraction on the first sample time-frequency feature maps of the at least two first sample electrode signals through a first convolutional layer in an EEG signal classification model, to obtain a first sample extracted feature map, the first sample extracted feature map being fused with spatial features of the at least two first sample electrode signals, and the spatial features of the at least two first sample electrode signals being related to spatial regions corresponding to the at least two first sample electrode signals;

performing, based on an attention weighted network in the EEG signal classification model, weighting processing based on an attention mechanism on the first sample extracted feature map to obtain an attention feature map of the first sample EEG signal;

obtaining a sample probability distribution of the first sample EEG signal based on the attention feature map of the first sample EEG signal, the sample probability distribution indicating probabilities that the first sample EEG signal is of each of a plurality of motor imagery types, respectively; and training the EEG signal classification model based on the sample probability distribution and a motor imagery type of the first sample EEG signal, the EEG signal classification model being configured to predict a motor imagery type of a first EEG signal.

9. The method according to claim 8, wherein the method further comprises:

obtaining a second sample EEG signal, the second sample EEG signal comprising at least two second sample electrode signals, and a second sample electrode signal indicating an EEG signal generated in a spatial region corresponding to the second sample electrode signal from a target object that performs motor imagery;

obtaining second sample time-frequency feature maps of the at least two second sample electrode signals, a second sample time-frequency feature map indicating a time-domain feature and a frequency-domain feature of the second sample electrode signal;

performing feature extraction on the second sample time-frequency feature maps of the at least two second sample electrode signals through the first convolutional layer in the EEG signal classification model, to obtain a second sample extracted feature map, the second sample extracted feature map being fused with spatial features of the at least two second sample electrode signals, and the spatial features of the at least two second sample electrode signals being related to spatial regions corresponding to the at least two second sample electrode signals; and performing, based on the attention weighted network in the EEG signal classification model, weighting processing based on the attention mechanism on the second sample extracted feature map to obtain the attention feature map of the second sample EEG signal; and the training the EEG signal classification model based on the sample probability distribution and the motor imagery type of the first sample EEG signal comprises:

training the EEG signal classification model based on the sample probability distribution, the motor imagery type of the first sample EEG signal, the attention feature map of the first sample EEG signal, and the attention feature map of the second sample EEG signal.

10. The method according to claim 9, wherein the second sample EEG signal indicates EEG signals generated by a target object corresponding to the first sample EEG signal at different moments;

or the second sample EEG signal indicates an EEG signal generated by an object other than the target object corresponding to the first sample EEG signal.

11. An EEG signal classification apparatus, comprising:

at least one memory configured to store program code; and at least one processor configured to read the program code and operate as instructed by the program code, the program code including:

first signal obtaining code configured to cause the at least one processor to obtain a first EEG signal; the first EEG signal comprising at least two electrode signals, and an electrode signal indicating an EEG signal generated by a target object in a spatial region corresponding to the electrode signal;

first time-frequency feature obtaining code configured to cause the at least one processor to obtain time-frequency feature maps of the at least two electrode signals, a time-frequency feature map indicating a time-domain feature and a frequency-domain feature of the electrode signal;

first extracted feature obtaining code configured to cause the at least one processor to perform feature extraction based on the time-frequency feature maps of the at least two electrode signals through a first convolutional layer in an EEG signal classification model to obtain a first extracted feature map, the first extracted feature map being fused with spatial features of the at least two electrode signals, and the spatial features of the at least two electrode signals being related to spatial regions corresponding to the at least two electrode signals;

first attention feature obtaining code configured to cause the at least one processor to perform, based on a first attention weighted network in the EEG signal classification model, weighting processing based on an attention mechanism on the first extracted feature map to obtain an attention feature map of the first EEG signal; and imagery type obtaining code configured to cause the at least one processor to obtain a motor imagery type of the first EEG signal based on the attention feature map of the first EEG signal, wherein the EEG signal classification model is trained based on a motor imagery type corresponding to a first sample EEG signal and a sample probability distribution corresponding to the first sample EEG signal, the sample probability distribution indicating probabilities that the first sample EEG signal is of each of various motor imagery types, respectively.

12. The apparatus according to claim 11, wherein the attention mechanism comprises at least one of a spatial attention mechanism or a channel attention mechanism.

13. The apparatus according to claim 12, wherein the first attention weighted network comprises a first spatial attention weighted network, a second convolutional layer, a first channel attention weighted network, and a third convolutional layer; and the attention feature obtaining code comprises:

first spatial weighted sub-code configured to cause the at least one processor to perform, based on the first spatial attention weighted network, weighting processing based on the spatial attention mechanism on the first extracted feature map to obtain a first spatial feature map;

second feature obtaining sub-code configured to cause the at least one processor to perform feature extraction on the first spatial feature map based on the second convolutional layer to obtain a second extracted feature map;

first channel weighted sub-code configured to cause the at least one processor to perform, based on the first channel attention weighted network, weighting processing based on the channel attention mechanism on the second extracted feature map to obtain a first channel feature map;

third feature obtaining sub-code configured to cause the at least one processor to perform feature extraction on the first channel feature map based on the third convolutional layer to obtain a third extracted feature map; and attention feature obtaining sub-code configured to obtain the attention feature map based on the first spatial feature map, the first channel feature map, and the third extracted feature map.

14. The apparatus according to claim 13, wherein the first attention weighted network further comprises a second attention weighted network; and the attention feature obtaining sub-code further comprises:

first fusion sub-code configured to cause the at least one processor to fuse the first spatial feature map, the first channel feature map, and the third extracted feature map to obtain a first fused feature map; and first attention weighted sub-code configured to cause the at least one processor to perform, through the second attention weighted network, weighting processing based on the attention mechanism on the first fused feature map to obtain the attention feature map.

15. The apparatus according to claim 14, wherein the second attention weighted network comprises a second spatial attention weighted network and a second channel attention weighted network; and the first attention weighted sub-code comprises:

first performing code configured to cause the at least one processor to perform, through the second channel attention weighted network, weighting processing based on the channel attention mechanism on the first fused feature map to obtain a second channel feature map; and second performing code configured to cause the at least one processor to perform, through the second spatial attention weighted network, weighting processing based on the spatial attention mechanism on the second channel feature map to obtain the attention feature map.

16. The apparatus according to claim 11, wherein the first time-frequency feature obtaining code is configured to cause the at least one processor to perform continuous wavelet transform based on the at least two electrode signals to obtain the time-frequency feature maps of the at least two electrode signals.

17. A computer device, comprising a processor and a memory, the memory storing at least one computer instruction, and the at least one computer instruction being loaded and executed by the processor to implement the EEG signal classification method according to claim 1.

18. A non-transitory computer-readable storage medium, storing at least one computer instruction, the at least one computer instruction being loaded and executed by a processor to implement the EEG signal classification method according to claim 1.

* * * * *